US007169894B2

(12) United States Patent
Martin

(10) Patent No.: US 7,169,894 B2
(45) Date of Patent: Jan. 30, 2007

(54) METHODS AND COMPOSITIONS FOR REVERSE TRANSLATION

(75) Inventor: Mark T. Martin, Rockville, MD (US)

(73) Assignee: Mirari Biosciences, Inc., Rockville, MD (US)

( * ) Notice: Subject to any disclaimer, the term of this patent is extended or adjusted under 35 U.S.C. 154(b) by 553 days.

(21) Appl. No.: 10/286,796

(22) Filed: Nov. 4, 2002

(65) Prior Publication Data

US 2003/0100000 A1 May 29, 2003

Related U.S. Application Data

(60) Provisional application No. 60/331,299, filed on Nov. 14, 2001.

(51) Int. Cl.
| | | |
|---|---|---|
| *C07K 1/00* | (2006.01) | |
| *C07K 14/00* | (2006.01) | |
| *C07K 17/00* | (2006.01) | |
| *G01N 33/53* | (2006.01) | |
| *C07H 21/04* | (2006.01) | |

(52) U.S. Cl. .................. 530/350; 435/7.1; 536/24.1; 930/10

(58) Field of Classification Search ................ None
See application file for complete search history.

(56) References Cited

U.S. PATENT DOCUMENTS

| 4,551,797 A | 11/1985 | Amdahl et al. ............. 364/200 |
| 5,541,342 A | 7/1996 | Korhonen et al. .......... 548/532 |
| 5,786,428 A | 7/1998 | Arnold et al. .............. 548/532 |
| 5,843,701 A | 12/1998 | Gold et al. ................ 435/68.1 |
| 6,846,638 B2 * | 1/2005 | Shipwash .................. 435/7.1 |

OTHER PUBLICATIONS

Agrawal, S. (1993) Protocols for Oligonucleotides and Analogs. Humana Press, Totowa, NJ, index only.
Agrawal, S. (1994) Protocols for Oligonucleotide Conjugates. Humana Press, Totowa, NJ.
Ahern, K. (2001) "Variations on PCR for the Amplification of DNA," Genetic Engineering News 21, 9.
Andersson, L.I. (2000) "Molecular Imprinting For Drug Bioanalysis. A Review On The Application Of Imprinted Polymers To Solid-Phase Extraction And Binding Assay," J. Chromatogr. B 739, 163-173.
Andersson, L.I. et al. (1990a) "Enantiomeric Resolution Of Amino Acid Derivatives On Molecularly Imprinted Polymers As Monitored By Potentiometric Measurements," J. Chromatogr. 516, 323-331.
Andersson, L.I. et al. (1990b) "Molecular Recognition In Synthetic Polymers: Preparation Of Chiral Stationary Phases By Molecular Imprinting Of Amino Acid Amides," J. Chromatogr. 513, 167-179.
Anonymous, Product Catalog and technical literature, Glen Research Corporation, Sterling, VA, 1999.
Avers, C.J. (1976) "Cell Biology," Van Nostrand, New York, index only.

Bhown, A.S. (1987) "Protein/Peptide Sequence Analysis: Current Methodologies," Protein/Peptide Sequence Analysis: Current Methodologies, CRC Press, Boca Raton, FL, index only.
Biro, J. (1983) "Information Transfer in Biological Systems," Med. Hypotheses 12, 31-40.
Blackstock, W.P. & Weir, M.P. (1999) "Proteomics: Quantitative and Physical Mapping of Cellular Proteins," Trends Biotechnol. 17, 121.
Braco, L. et al. (1990) "Production Of Abiotic Receptors By Molecular Imprinting Of Proteins," Proc. Natl. Acad. Sci., USA 87, 274-277.
Cook, N.D. (1977) "The Case for Reverse Translation," J. Theor. Biol. 64, 113.
Craig, R. (1981) "The Theoretical Possibility Of Reverse Translation Of Proteins Into Genes," J. Theor. Biol. 88, 760.
Dai, S. et al. (1999) "Imprint Coating: A Novel Synthesis of Selective Functionalized Ordered Mesoporous Sorbents," Angew. Chem. Int. Ed. 38, 1235.
Dhal, P.K. et al. (1995) "Surface Grafting of Functional Polymers to Macroporous Poly(trimethylolpropane) trimethacrylate)," Chem. Mater. 7, 154-162.
Dickert, FL & Thierer S (1996) "Molecularly Imprinted Polymers for Optochemical Sensors," Adv. Mater. 8, 987.
Dove, A. (1999) "Proteomics: Translating Genomics into Products," Nature Biotechnol. 17, 233.
Dupont, D.R. et al. (2000) "The Alkylated Thiohydantoin method for C-terminal Sequence Analysis," EXS 88, 119-131.
Eckstein, F. (1991) Oligonucleotides and Analogues, A Practical Approach. IRL Press, New York.
Findlay, JBC & Geisow, MJ Protein Sequencing. A Practical Approach, Oxford University Press, New York. p. 121-123.
Freitag, R. & Vogt, S. (2000) "Comparison Of Particulate And Continuous-Bed Columns For Protein Displacement Chromatography," J. Biotechnol. 78, 69-72.
Frenz, J. (1996) "Trace Analysis Peptide Mapping be High-Performance Displacement Chromatography," Meth. Enzymol. 271, 486-504.
Gevaert, K. et al. (2000) "Techniques for Sample Preparation Including Methods for Concentrating Peptide Samples," EXS 88, 29-42.
Guillier, F. et al. (2000) "Linkers And Cleavage Strategies In Solid-Phase Organic Synthesis And Combinatorial Chemistry," Chem. Rev. 100, 2091-2157.

(Continued)

*Primary Examiner*—Teresa E. Strzelecka
(74) *Attorney, Agent, or Firm*—Jenkins, Wilson, Taylor & Hunt, P.A.

(57) ABSTRACT

A process is disclosed by which a polynucleotide is directly synthesized from the peptide or protein that it encodes without the need for sequencing (or sequence analysis) of the peptide or protein. Information contained in the sequence of the peptide or protein is directly coupled, by the process of reverse translation, to the synthesis of the polynucleotide. The usefulness of reverse translation is that it facilitates the amplification of information held in the amino acid sequence (the primary structure) of an unknown protein or peptide. Amplification is useful for, among other things, the identification and/or scientific investigation of the peptide or protein.

25 Claims, 19 Drawing Sheets

OTHER PUBLICATIONS

Hames, B.D. Gel Electrophoresis of Proteins: A Practical Approach. Oxford Univ. Press, New York, 1988, p. 189-228.

Hancock, W.S. CRC Handbook of HPLC For the Separation of Amino Acids, Peptides, and Proteins. CRC Press, Boca Raton, Florida, 1984, p. 376-379.

Harlow, E. & Lane, D. (1988) "" Antibodies. A Laboratory Manual, Cold Spring Harbor Laboratory, Cold Spring Harbor, NY, index only.

Haugland, R.P. (1996) "," Handbook of Fluroescent Probes and Research Chemicals. Molecular Probes, Inc., Eugene, OR, index only.

Haupt, K. & Mosbach, K. (2000) "Molecularly Imprinted Polymers And Their Use In Biomimetic Sensors," Chem. Rev. 100, 2495-2504.

Hellman, U. (2000) "Sample Preparation By SDS/PAGE And In-Gel Digestion," EXS 88, 43-54.

Hermanson, G.T. (1996) Bioconjugate Techniques, Academic Press, New York, p. 303, 304, 368, 369, 666, 667.

Hermanson, G.T. et al. (1992) Immobilized Affinity Ligand Techniques. Academic Press, New York, index.

Honore, B & Madsen, P. (1997) "The Tetramethylammonium Chloride (TMAC) Method For Screening cDNA Libraries With Highly Degenerate Oligonucleotide Probes Obtained By Reverse Translation Of Amino Acid Sequences," Methods Mol. Biol. 69, 139.

Humphery-Smith et al. (1997) "Proteome Research: Complementarity And Limitations With Respect To The RNA And DNA Worlds," Electrophoresis 18, 1217.

Inglis, A.S. (1991) "Chemical Procedures For C-Terminal Sequencing Of Peptides And Proteins," Anal. Biochem. 195, 183-196.

International Human Genome Sequencing Consortium (2001) "Initial Sequencing and Analysis of the Human Genome," Nature 409, 860.

Irving, M.B. et al. (2001) "Random-Peptide Libraries And Antigen-Fragment Libraries For Epitope Mapping And The Development Of Vaccines And Diagnostics," Curr. Opin. Chem. Biol. 5, 314-24.

Kalghatgi, K. et al. (1992) "Rapid Displacement Chromatography Of Melittin On Micropellicular Octadecyl-Silica," J. Chromatogr. 604, 47-53.

Katz, A. & Davis, M.E. (2000) "Molecular Imprinting of Bulk Microporous Silica," Nature 403, 286-289.

Kempe, M. & Mosbach, K. (1995) "Separation Of Amino Acids, Peptides, And Proteins On Molecularly Imprinted Stationary Phases," J. Chromatogr. A 691, 317.

Kirsch, N. et al. (2000) "Enhancement Of Selectivity Of Imprinted Polymers Via Post-Imprinting Modification Of Recognition Sites," Polymer 41, 5583-5590.

Klein, J.U. et al. (1999) "Template-Mediated Synthesis Of A Polymeric Receptor Specific To Amino Acid Sequences," Angew. Chem. Int. 38, 2057-60.

Kloor, D. et al. (2000) "Simple And Sensitive Binding Assay For Measurement Of Adenosine Using Reduced S-Adenosylhomocysteine Hydrolase," Clin. Chem 46, 537-542.

Kundu, A. et al. (1995) "Protected Amino Acids As Novel Low Molecular Weight Displacers In Cation-Exchange Displacement Chromatography," Biotechnol. Bioengin. 48, 452-460.

Lahm, H.-W. & Langen, H. (2000) "Mass Spectrometry: A Tool For The Identification Of Proteins Separated By Gels," Electrophoresis 21, 2105-2114.

Lee, S.-W. et al. (1998) "Molecular Imprinting Of Protected Amino Acids In Ultrathin Multilayers Of $Tio_2$ Gel," Chem. Lett. (12) "," 1193-1194.

Lehninger, A.L. (1975) Biochemistry, 2nd Ed., Worth Publishers, Inc. New York, index only.

Leonhardt, A. & Mosbach, K. (1987) "Enzyme-Mimicking Polymers Exhibiting Specific Substrate Binding And Catalytic Functions," Reactive Polymers 6, 285.

Lottspeich et al. "Amino Acid Analysis in Microscale," in Cell Biology: A Laboratory Handbook, 2nd Ed, New York, 1998, JE Celis, ed. p. 304.

Mallik, S. et al. (1994) "Towards Materials for the Specific Recognition and Separation of Proteins," New J. Chem. 18, 299-304.

Mathew, J. & Burchardt, O. (1995) "Molecular Imprinting Approach for the Recognition of Adenine in Aqueous Medium and Hydrolysis of Adenosine 5'-Triphosphate," Bioconjugate Chem. 6, 524-528.

Mathew-Krotz, J. et al. (1995) "Imprinted Polymer Membranes For The Selective Transport Of Targeted Neutral Molecules," J. Am. Chem. Soc. 118, 8134-8135.

Means, G.E. & Feeney, R.E. (1971) Chemical Modification of Proteins, Holden-Day, San Francisco, index only.

Mekler, L.B. (1967) "Mechanism of Biological Memory," Nature 215, 481-4.

Miyahara, T. & Kurihara, K. (2001) "Two-Dimensional Molecular Imprinting: Binding of Sugars to Boronic Acid Functionalized, Polymerized Langmuir-Blodgett Films," Chem. Lett. (12) "," 1356-1357.

Nashimoto, M. (2001) "The RNA/Protein Symetry Hypothesis: Experimental Support for reverse Translation of Primitive Proteins," J. Theor. Biol. 209, 181-187.

Ngo, T.T. (1993) Molecular Interactions in Bioseparations, Plenum Press, New York, index only.

O'Shannessy et al. (1989a), "Molecular Imprinting of Amino Acid Derivatives at Low Temperature (0°C) using Photolytic Homolysis of Azobisnitriles," Anal. Biochem. 177, 144.

O'Shannessy et al. (1989b), "Recent Advances in the Preparation and Use of Molecularly Imprinted Polymers for Enantiomeric Resolution of amino Acid Derivatives," J. Chromatogr. (1989b) 470, 391.

O'Shannessey, D.J. et al. (1989b) "Molecular Recognition in Synthetic Polymers," J. Mol. Recognition 2, 1-5.

Odian, G. (1991) Principles of Polymerization, 3rd Ed., Wiley & Sons, New York, index only.

Ohkubo, K. et al. (1994) "Preparation and Catalytic Property Of L-Histidyl Group Introduced, Crosslinked Poly(Ethylene lmine) Imprinted By A Transition-State Analogue Of An Esterolysis Reaction," Polymer 35, 5372-5375.

Paul, S. (1995) "," Antibody Engineering Protocols, Humana Press, Totowa, NJ, index only.

Quadroni, M. & James, P. (1999) "Proteomic and Automation," Electrophoresis 20, 664-677.

Rabilloud, T. Proteome Research: Two Dimensional Gel Electrophoresis and Identification Methods. Springer, New York, 2000, index only.

Rachkov, A. et al. (2000) "Fluorescence Detection Of Beta-Estradiol Using A Molecularly Imprinted Polymer," Anal. Chim. Acta 405, 23-29.

Ramstrom, O. et al. (1993) "Recognition Sites Incorporating Both Pyridinyl and Carboxy Functionalities Prepared by Molecular Imprinting," J. Org. Chem. 58, 7562-4.

Ray, A. & Gupta, S.N. (1997) "Construction Of Template Ligand Sites In Polymeric Matrices In Dithizone,"J. Polmer Sci. part A: Polymer Chemistry, J. Polymer Science: Part A: Polymer Chemistry. 35, 3729-3734.

Salzberg, S.L. et al. (2001) "Microbial Genes in the Human Genome: Lateral Transfer or Gene Loss," Science 292, 1903-1906.

Sambrook, J. et al. (1989) Molecular Cloning: A Laboratory Manual 2nd Ed, Cold Spring Harbor, NY. Chapter 11. Crosslinkers and Activation, 11.3-11.18 and 11.56-11.60.

Sambrook, J. et al. (2001) Molecular cloning: a laboratory manual. Cold Spring Harbor Laboratory Press, Cold Spring Harbor, NY, index only.

Saunders, K.J. (1988) Organic Polymer Chemistry, Chapman and Hall, New York, p. 125-148.

Sblattero, D. et al. (2001) "In Vivo Recombination As A Tool To Generate Molecular Diversity In Phage Ntibody Libraries," J. Biotechnol. 74, 303-315.

Schmidt, B. et al. (1999) "Polycations As Displacer In High Performance Bioseparation," J. Chromatogr. A 865, 27-34.

Sellergren, B. (1997) "Imprinted Polymers: Stable, Reusable Antibody Mimics For Highly Selective Separations," Int. Laboratory, Jul. 10A-10F.

Shea, K.J. (1994) "Molecular Imprinting of Synthetic Network Polymers: The De Novo Synthesis of Macromolecular Binding and Catalytic Sites," Trends Polymer Science 2, 166-173.

Shea, K.J. et al. (1993) "Polymer Complements to nucleotide Bases. Selective Binding of Adenine Derivatives to Imprinted Polymers," J. Am. Chem. Soc. 115, 3368-3369.

Shi, H. et al. (1999) "Template-Imprinted Nanostructured Surfaces for Protein Recognition," Nature 398, 593-597.

Shiuan, D. et al. (1997) "Competitive Enzyme-Linked Immunosorbent Assay for Biotin," Meth. Enzymol. 279, 321-326.

Shively, J.E. (2000) "The Chemistry of Protein Sequence Analysis," EXS 88, 99-117.

Shukla, A.A. et al. (2000) "Hydrophobic Displacement Chromatography of Proteins," Biotechnol. Bioengin. 68, 672-679.

Soderlind, E. et al. (2001) "The Immune Diversity In A Test Tube—Non-Immunised Antibody Libraries And Functional Variability In Defined Protein Scaffolds," Comb. Chem. High Throughput Screen. 4:409-16.

Spivak, D. & Shea, K.J. (1998) "Binding of Nucleotide Bases by Imprinted Polymers," Macromolecules 31, 2160-2165.

Spivak, D. et al. (1997) "Evaluation of Binding and Origins of Specificity of 9-Ethyladenine Imprinted Polymers," J. Am. Chem. Soc. 119, 4388-4393.

Trevors, J.T. (2001) "Molecular Evolution: First Enzymes, Gases as substrates and Genetic Templates," Rivista di Biologia/Biology Forum 94, 105-122.

Venter, J.C. et al. (2001) "The Sequence of the Human Genome," Science 291, 1304.

Vlatakis, G. et al. (1993) "Drug Assay Using Antibody Mimics made by Molecular Imprinting," Nature 361, 645.

Wang, C. et al. (2000) "Integration Of Immobilized Trypsin Bead Beds For Protein Digestion Within A Microfluidic Chip Incorporating Capillary Electrophoresis Separations And An Electrospray Mass Spectrometry Interface," Rapid Commun. Mass Spectrometry 14, 1377-1383.

Wold, F. (1981) "In vitro Chemical Modification of Proteins," Ann. Rev. Biochem. 50, 783-814.

Wong, S.H. (1991) "Chemistry of Protein Conjugation and Cross-Linking," Chemistry of Protein Cross-linking and Crosslinking, CRC Press, Boston, index only.

Wulff, G. (1998) "Fitting Molecules into Polymeric Receptors," ChemTech, Nov. 19-26.

Wurzel, C. & Wittmann-Liebold, B. (2000) "New Approaches for Innovations in Sensitive Edman Sequence Analysis by Desigh of a Wafer-Based Chip Sequencer," EXS 88, 145-157.

Yan, M. and Kapua, A. (2001) "Fabrication of Molecularly Imprinted Polymer Microstructures," Anal. Chim. Acta 435, 163-7.

Ye, L. et al. (2001) "Molecular Imprinting on Microgel Spheres," Anal. Chem. Acta 435, 187-196.

Yoshikawa, M. et al. (2001) "Recognition and Selective Transport of Nucleic Acid Components through Molecularly Imprinted Polymeric Membranes," Macromol. Mater. Eng. 286, 52-59.

Zhou, J., He, X., & Li, Y. (1999) "An Acrylamide-Based Molecularly Imprinted Polymer For The Efficient Recognition Of Opticalamino Acid Hydantoins," Anal. Chim. Acta 394, 353-359.

Zhou, J., He, X., & Li, Y. (1999) "Binding Study On 5,5 Diphenylhydantoin Imprinted Polymer Constructed By Utilizing An Amide Functional Group," Anal. Commun. 36, 243-6.

* cited by examiner

Figure 1

Second Nucleotide

First Nucleotide / Third Nucleotide

| | A or U | G or C | T or A | C or G | |
|---|---|---|---|---|---|
| A or U | Phenylalanine<br>AAA UUU<br>AAG UUC<br><br>Leucine<br>AAT UUA<br>AAC UUG | Serine<br>AGA UCU<br>AGG UCC<br>AGT UCA<br>AGC UCG | Tyrosine<br>ATA UAU<br>ATG UAC<br><br>"Stop"<br>ATT UAA<br>ATC UAG | Cysteine<br>ACA UGU<br>ACG UGC<br><br>"Stop"<br>ACT UGA<br><br>Tryptophan<br>ACC UGG | A or U<br>G or C<br>T or A<br>C or G |
| G or C | Leucine<br>GAA CUU<br>GAG CUC<br>GAT CUA<br>GAC CUG | Proline<br>GGA CCU<br>GGG CCC<br>GGT CCA<br>GGC CCG | Histidine<br>GTA CAU<br>GTG CAC<br><br>Glutamine<br>GTT CAA<br>GTC CAG | Arginine<br>GCA CGU<br>GCG CGC<br>GCT CGA<br>GCC CGG | A or U<br>G or C<br>T or A<br>C or G |
| T or A | Isoleucine<br>TAA AUU<br>TAG AUC<br>TAT AUA<br><br>Methionine<br>TAC AUG | Threonine<br>TGA ACU<br>TGG ACC<br>TCT ACA<br>TGC ACG | Asparagine<br>TTA AAU<br>TTG AAC<br><br>Lysine<br>TTT AAA<br>TTC AAG | Serine<br>TCA AGU<br>TCG AGC<br><br>Arginine<br>TCT AGA<br>TCC AGG | A or U<br>G or C<br>T or A<br>C or G |
| C or G | Valine<br>CAA GUU<br>CAG GUC<br>CAT GUA<br>CAC GUG | Alanine<br>CGA GCU<br>CGG GCC<br>CGT GCA<br>CGC GCG | Aspartic Acid<br>CTA GAU<br>CTG GAC<br><br>Glutamic Acid<br>CTT GAA<br>CTC GAG | Glycine<br>CCA GGU<br>CCG GGC<br>CCT GGA<br>CCC GGG | A or U<br>G or C<br>T or A<br>C or G |

Figure 2
*Step 1.* Stepwise cleavage of a PAA of arbitrary (a) sequence and length
a-a-a-a-a-a-a-a-a   ⟶   a-a-a-a-a-a-a-a  +  a
*Step 2.* Amino acid-for-codon exchange
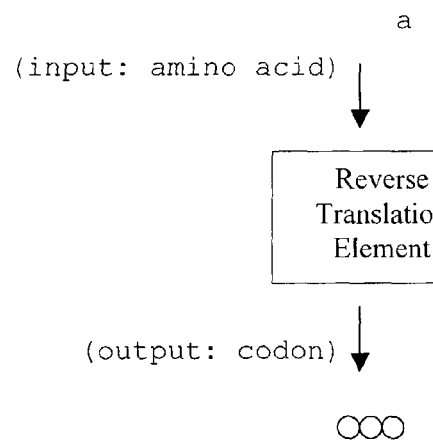
*Step 3.* Oligonucleotide Synthesis
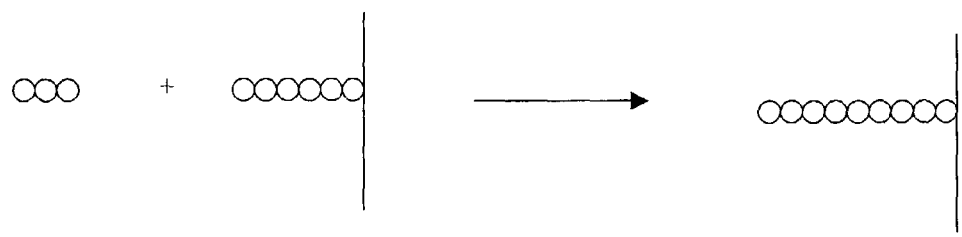

Figure 4
| Reagent(s) | Degradation Product (R is amino acid sidechain) |
|---|---|
| 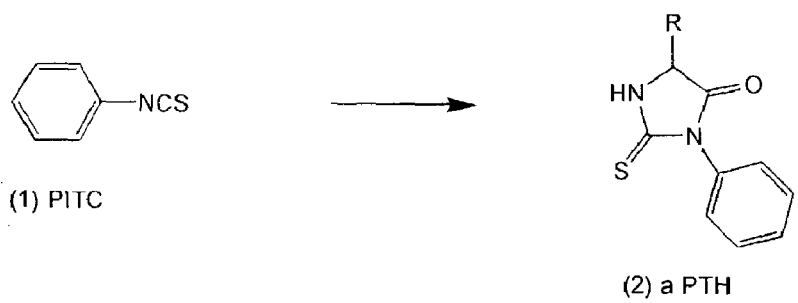 (1) PITC | (2) a PTH |
| 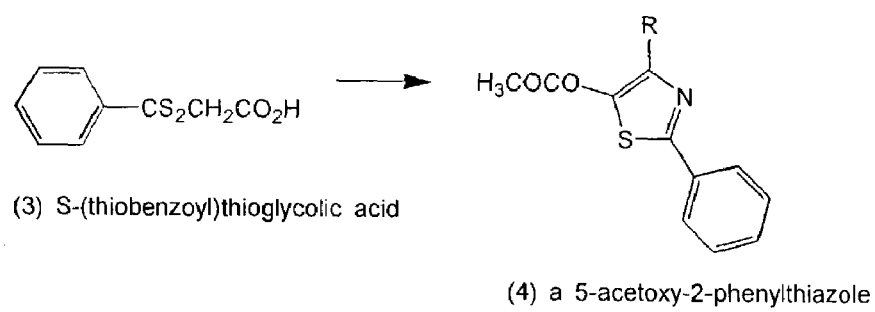 (3) S-(thiobenzoyl)thioglycolic acid | (4) a 5-acetoxy-2-phenylthiazole |
| 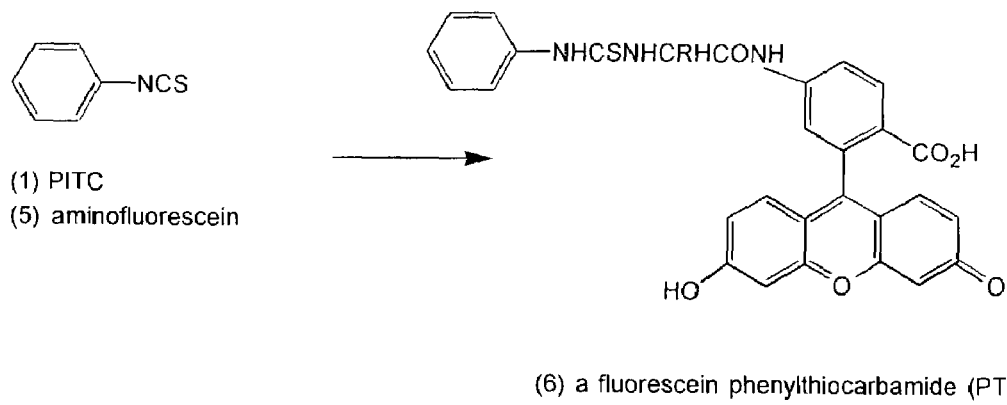 (1) PITC (5) aminofluorescein | (6) a fluorescein phenylthiocarbamide (PTCAF) |
| 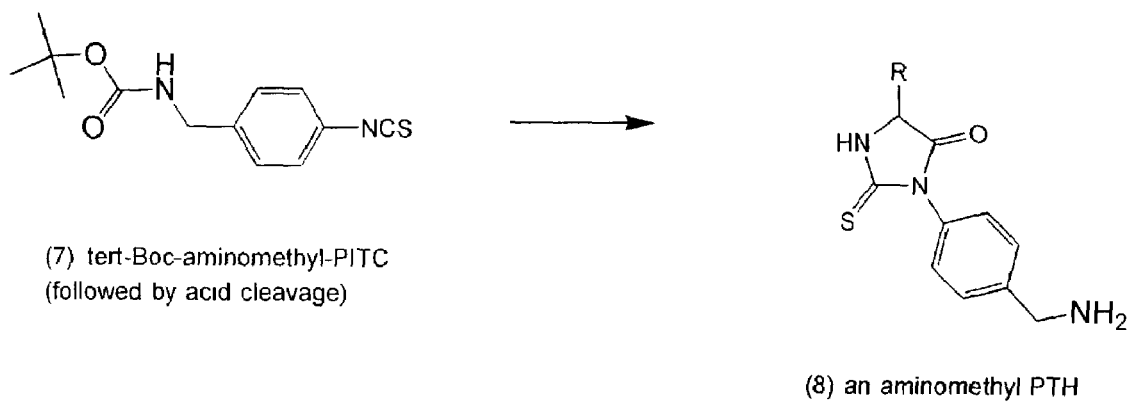 (7) tert-Boc-aminomethyl-PITC (followed by acid cleavage) | (8) an aminomethyl PTH |

Figure 6A

| HUMAN | HUMAN MITOCHONDRON | MOUSE (Mus muscularus) | E. coli |
|---|---|---|---|
| Phenylalanine | | | |
| UUU 17.0 | UUU 16.2 | UUU 16.0 | UUU 21.9 |
| UUC 20.5 | UUC 35.1 | UUC 21.6 | UUC 16.4 |
| Leucine | | | |
| UUA 7.3 | UUA 16.8 | UUA 6.0 | UUA 13.9 |
| UUG 12.5 | UUG 5.4 | UUG 12.5 | UUG 13.1 |
| CUU 12.8 | CUU 19.7 | CUU 12.3 | CUU 11.2 |
| CUC 19.3 | CUC 36.7 | CUC 19.6 | CUC 10.3 |
| CUA 7.0 | CUA 66.0 | CUA 7.5 | CUA 4.0 |
| CUG 39.7 | CUG 14.4 | CUG 39.3 | CUG 50.4 |
| Isoleucine | | | |
| AUU 15.8 | AUU 32.8 | AUU 14.6 | AUU 30.1 |
| AUC 21.6 | AUC 53.9 | AUC 22.9 | AUC 24.4 |
| AUA 7.2 | AUA 42.9 | AUA 6.6 | AUA 5.6 |
| Methionine | | | |
| AUG 22.3 | AUG 11.3 | AUG 22.2 | AUG 26.8 |
| Valine | | | |
| GUU 10.9 | GUU 8.4 | GUU 10.1 | GUU 19.6 |
| GUC 14.6 | GUC 18.0 | GUC 15.6 | GUC 14.6 |
| GUA 7.0 | GUA 19.0 | GUA 6.9 | GUA 11.4 |
| GUG 28.8 | GUG 6.6 | GUG 29.0 | GUG 25.2 |
| Serine | | | |
| UCU 14.8 | UCU 8.1 | UCU 15.4 | UCU 9.9 |
| UCC 17.5 | UCC 22.3 | UCC 18.1 | UCC 9.1 |
| UCA 11.9 | UCA 19.8 | UCA 11.2 | UCA 8.1 |
| UCG 4.5 | UCG 1.9 | UCG 4.5 | UCG 8.6 |
| AGU 12.0 | AGU 3.4 | AGU 12.2 | AGU 9.2 |
| AGC 19.3 | AGC 7.3 | AGC 20.0 | AGC 15.3 |
| Prol,ine | | | |
| CCU 17.3 | CCU 9.3 | CCU 18.7 | CCU 7.2 |
| CCC 20.0 | CCC 33.8 | CCC 19.1 | CCC 5.1 |
| CCA 16.7 | CCA 12.1 | CCA 17.3 | CCA 8.6 |
| CCG 7.0 | CCG 3.8 | CCG 6.8 | CCG 22.0 |
| Threonine | | | |
| ACU 12.9 | ACU 15.5 | ACU 13.2 | ACU 10.0 |
| ACC 19.3 | ACC 40.1 | ACC 19.6 | ACC 22.8 |
| ACA 14.9 | ACA 32.0 | ACA 15.6 | ACA 8.2 |
| ACG 6.3 | ACG 2.6 | ACG 6.1 | ACG 13.8 |

Figure 6B

| HUMAN | HUMAN MITOCHONDRON | MOUSE (Mus muscularus) | E. coli |
|---|---|---|---|
| Alanine | | | |
| GCU 18.5 | GCU 14.0 | GCU 19.7 | GCU 16.8 |
| GCC 28.3 | GCC 31.8 | GCC 26.7 | GCC 24.5 |
| GCA 15.9 | GCA 22.1 | GCA 15.5 | GCA 21.0 |
| GCG 7.5 | GCG 3.7 | GCG 7.1 | GCG 31.8 |
| Tyrosine | | | |
| UAU 12.1 | UAU 11.1 | UAU 11.8 | UAU 16.9 |
| UAC 15.8 | UAC 24.9 | UAC 16.8 | UAC 12.3 |
| Histidine | | | |
| CAU 10.5 | CAU 5.2 | CAU 9.9 | CAU 12.6 |
| CAC 14.9 | CAC 17.7 | CAC 15.3 | CAC 9.6 |
| Glutamine | | | |
| CAA 12.0 | CAA 20.6 | CAA 11.6 | CAA 14.7 |
| CAG 34.5 | CAG 4.3 | CAG 34.5 | CAG 28.6 |
| Asparagine | | | |
| AAU 17.0 | AAU 10.0 | AAU 15.5 | AAU 19.2 |
| AAC 19.8 | AAC 32.0 | AAC 21.5 | AAC 21.8 |
| Lysine | | | |
| AAA 24.0 | AAA 21.0 | AAA 21.3 | AAA 34.8 |
| AAG 32.6 | AAG 2.6 | AAG 34.6 | AAG 11.5 |
| Aspartic Acid | | | |
| GAU 22.4 | GAU 5.9 | GAU 21.4 | GAU 32.6 |
| GAC 26.1 | GAC 19.0 | GAC 27.5 | GAC 19.5 |
| Glutamic Acid | | | |
| GAA 29.1 | GAA 20.2 | GAA 26.9 | GAA 39.7 |
| GAG 40.3 | GAG 9.8 | GAG 40.3 | GAG 18.2 |
| Cysteine | | | |
| UGU 10.0 | UGU 2.1 | UGU 10.9 | UGU 5.1 |
| UGC 12.3 | UGC 6.0 | UGC 12.6 | UGC 6.2 |
| Arginine | | | |
| CGU 4.6 | CGU 4.0 | CGU 4.7 | CGU 20.6 |
| CGC 10.8 | CGC 6.0 | CGC 10.1 | CGC 20.6 |
| CGA 6.3 | CGA 8.0 | CGA 6.7 | CGA 3.5 |
| CGG 11.6 | CGG 1.0 | CGG 10.5 | CGG 5.4 |
| AGA 11.5 | AGA 0.4 | AGA 11.4 | AGA 2.8 |
| AGG 11.3 | AGG 0.4 | AGG 11.6 | AGG 1.7 |
| Glycine | | | |
| GGU 10.8 | GGU 8.2 | GGU 11.7 | GGU 25.9 |
| GGC 22.7 | GGC 20.8 | GGC 22.9 | GGC 28.4 |
| GGA 16.4 | GGA 17.6 | GGA 17.3 | GGA 8.7 |
| GGG 16.4 | GGG 9.2 | GGG 15.9 | GGG 11.0 |

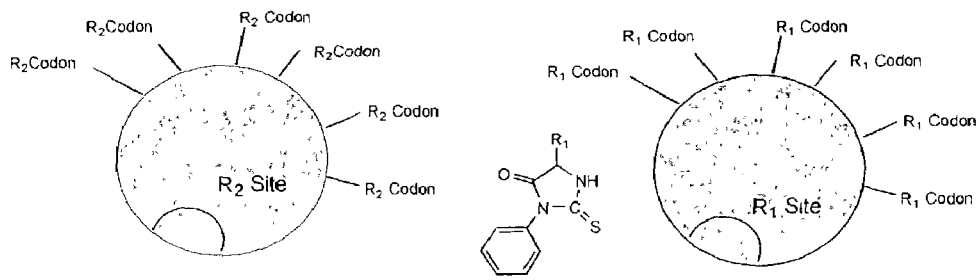
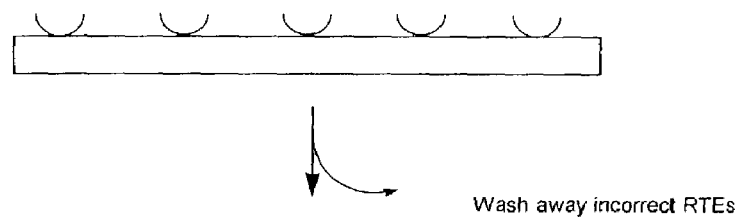
Wash away incorrect RTEs
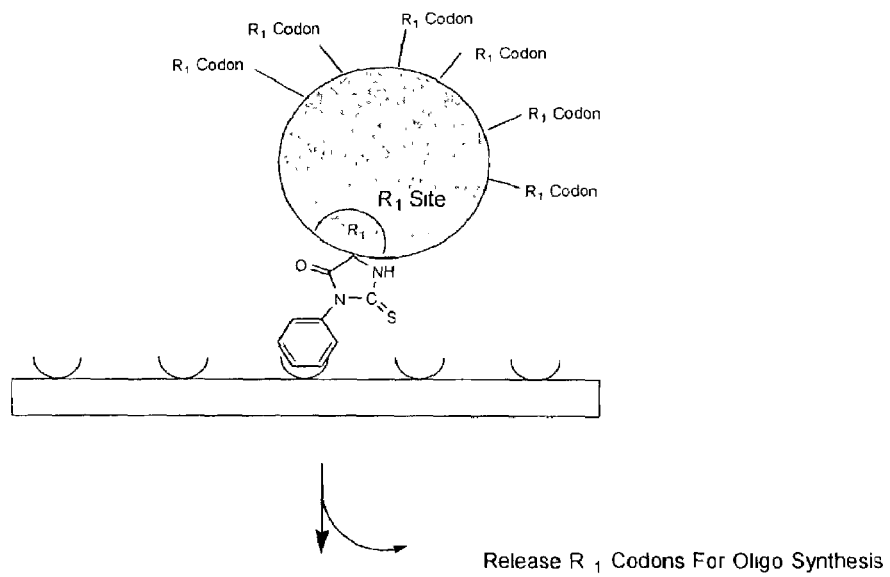
Release R₁ Codons For Oligo Synthesis
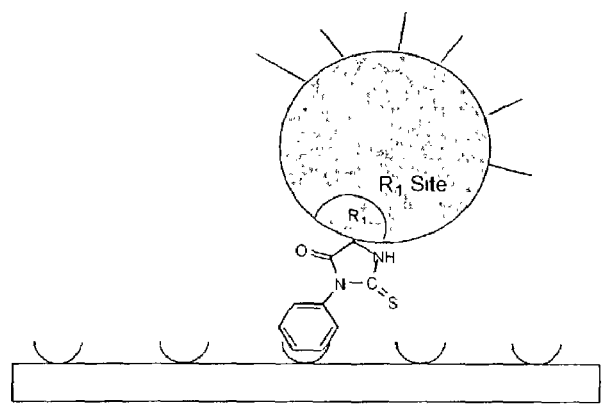
Figure 7

Displacement of Correct Codon

```
                            SEQUENCE LISTING

<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence:
      Hypothetical Sequence

<400> SEQUENCE: 1

Ala Ala Ala Ala Ala Ala Ala Ala Ala
 1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:
      Hypothetical Sequence

<400> SEQUENCE: 2

Ala Ala Ala Ala Ala Ala Ala Ala
 1               5
```

METHODS AND COMPOSITIONS FOR REVERSE TRANSLATION

CROSS-REFERENCE TO RELATED APPLICATIONS

This application claims priority to U.S. patent application Ser. No. 60/331,299, filed Nov. 14, 2001, herein incorporated by reference.

FIELD OF THE INVENTION

The present invention relates to poly-amino acid reverse translation: the process whereby a polynucleotide is synthesized directly from the peptide or protein that it encodes without the need for sequencing (or sequence analysis) of the peptide or protein. The invention falls within the technical fields of biochemistry, protein chemistry, nucleic acid chemistry, molecular imprinting, and bioconjugate chemistry.

BACKGROUND—DESCRIPTION OF PRIOR ART

The Central Dogma of Molecular Genetics is "DNA makes RNA makes protein" (Lehninger, 1975). Information in biological systems flows from DNA to RNA to protein. This is shown in the following scheme;

In addition, double-stranded DNA can be used as a template to make new DNA. In nature, DNA is usually synthesized from DNA in a process called DNA replication.

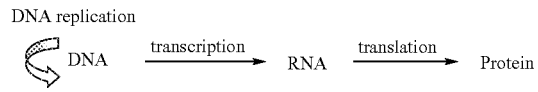

In nature, DNA can also be formed from an RNA template. This process, called reverse transcription, is catalyzed by viral enzymes known as reverse transcriptases.

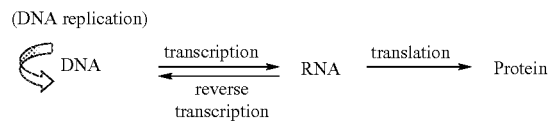

Notably, there is no known natural synthesis of RNA (or DNA) from a protein template, which could be considered "reverse translation". To be more precise, in this document the term poly-amino acid reverse translation (PAA-RT) is used to describe the process shown (see definitions, below).

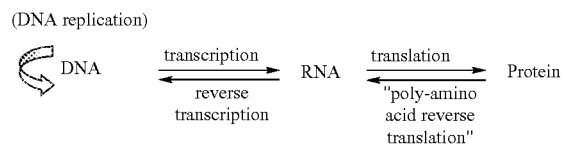

Not only has PAA-RT not been found in nature, it has not been carried out in the laboratory.

All of the processes described above, with the exception of PAA-RT, occur in nature. In addition, all of the processes described above, again with the exception of PAA-RT, are used in the biological research and development laboratory both in vivo and in vitro. In vivo applications involve the use of cells, commonly the bacterium *E. coli*, to produce protein from DNA, for example. In vitro studies often involve isolated enzymes. For example, transcription can be carried out using commercial kits (e.g., Promega Corp., Madison, Wis.). Similarly, reverse transcriptases, usually from avian myeloblastosis virus (AMV) or Moloney murine leukemia virus (MMLV), are used for reverse transcription (e.g., CLONTECH, Palo Alto, Calif.; Life Technologies, Inc., Rockville, Md.; New England Biolabs, Beverly, Mass.). In vitro translation can be carried out by eukaryotic (using rabbit reticulocyte lysates or wheat germ lysates) or prokaryotic (*E. coli*) systems (e.g., Promega Corp., Madison, Wis.). In addition, translation can be carried out using a novel system in which the encoding RNA and the growing peptide are linked in one chain (Phylos, Inc., Lexington, Mass.). Despite its high potential value, no reports of in vivo or in vitro PAA-RT exist.

Historically, there have been published speculations that PAA-RT may have existed in nature in molecular evolution, and indeed may exist undiscovered in nature today (Mekler, 1967; Cook, 1977; Craig, 1981; Biro, 1983; Trevors, 2001). All of these papers speculate on whether or not natural PAA-RT could have taken place and do not propose that PAA-RT could be carried out in the laboratory.

Two U.S. patents refer to reverse translation. One, Apparatus For Reverse Translation (U.S. Pat. No. 4,551,797), refers to data storage and has nothing to do with proteins or biotechnology. The other, Systematic Polypeptide Evolution By Reverse Translation (U.S. Pat. No. 5,843,701), uses the term reverse translation, but that invention does not describe a means of directly translating a peptide/protein into an oligo/polynucleotide. Instead, it describes a means of amplifying a peptide by using a covalent conjugate of the said peptide and its (already-synthesized) encoding mRNA. In the invention, the peptide portion of the peptide-RNA conjugate is captured and the mRNA is translating to form multiple copies of the peptide.

Recently a paper was published in which it was speculated that PAA-RT could be carried out in the laboratory (Nashimoto, 2001). The author suggested that PAA-RT might be carried out using designed RNA molecules and enzymes. An RNA molecule was designed and produced that bound the free amino acid, arginine, and the arginine-encoding codon, AGG. A self-cleavage reaction transferred the AGG codon to an acceptor RNA molecule. A number of critical steps in RT were not described. For example, not addressed or enabled were; how binding of the amino acid triggers RNA synthesis, how the peptide/protein would be "read" in sequence, and how the folded protein would be unfolded for PAA-RT to take place. In addition, PAA-RT "tools" (designed RNA molecules and specific enzymes) are required for each of the 20 amino acids, but the chemistry and/or molecular biology for making them is not disclosed in a way that would enable one skilled in the art to accomplish PAA-RT (only an arginine/AGG-binding RNA is disclosed). This is in stark contrast to the present invention, which describes PAA-RT in detail sufficient for one skilled in the art to perform the invention.

The present invention is the first description of a method of PAA-RT. The key component of the disclosed in vitro method for carrying out PAA-RT is the use of a so-called "Reverse Translation Element" (RTE). Amino acid derivatives are sequentially released from peptides/proteins. RTEs promote the exchange of these freed amino acid derivatives for their corresponding encoding trinucleotide codons. The codons are then sequentially coupled to the nascent peptide-encoding polynucleotide chain.

Until now, the synthesis of an encoding polynucleotide (RNA or DNA) that encodes a specific peptide or protein involved more than one process. Conventionally, a purified peptide or protein is sequenced using an automated amino acid sequencing machine. Following sequencing, the identity and order of the amino acids are read. From the sequence, an oligonucleotide is synthesized using a second instrument, an oligonucleotide synthesizer. Oligos may also be synthesized manually. From the prepared oligo, the full-length polynucleotide can be cloned. From the full-length polynucleotide, the protein can be produced. Drawbacks of this, the state of the art, procedure include; (1) it is time consuming, and (2) sufficient purified protein must be obtained for accurate amino acid sequencing.

OBJECT OF THE INVENTION

The object of this invention is to prepare and use compositions for poly-amino acid reverse translation (PAA-RT)—the transformation of a peptide or protein (poly-amino acid; PAA) sequence into an encoding polynucleotide (RNA or DNA) sequence.

One advantage of the invention is the ability to amplify extremely small amounts of PAA (theoretically down to a single molecule) to larger quantities. Once a PAA has been reverse translated into a nucleic acid, the nucleic acid can be amplified by polymerase chain reaction (PCR) or another amplification method. Amplified nucleic acid can be used to produce large amounts of the original PAA. Thus, PAA-RT can be thought of as "protein PCR".

A second advantage of the invention is that is a labor saving method. When cloning the gene of a discovered protein (of unknown sequence), PAA-RT obviates the steps of (i) determining the amino acid sequence of the unknown protein, then (ii) synthesizing degenerate oligonucleotides representing a peptide portion of that sequence. With PAA-RT, the peptide is directly translated to an oligonucleotide. The synthesized oligonucleotide can then be amplified and used to produce large amounts of the protein.

One practical application of the described invention is in the discovery of previously unknown peptides and proteins. The majority of all known and predicted proteins have no known cellular function. Discovering and/or determining the function of these proteins, especially on a genome-wide scale (the field of proteomics) provides critical answers to the understanding of metabolic processes. Importantly, since proteins are involved in all disease states (caused by viruses, bacteria, stress, and genetic mutations), complete descriptions of the structure and function of unknown proteins substantially aids in the understanding of disease processes and in the development of new therapies.

Another practical application of the invention is in the detection of known proteins. As a protein amplification method, small amounts of protein or peptides can be detected that would be invisible to other detection methods. This is valuable in diagnostic medicine, forensics, and other fields where peptide or protein analysis is valuable.

BRIEF DESCRIPTION OF THE FIGURES

FIG. 1: The genetic code.

FIG. 2: Diagram of the Components of poly-amino acid reverse translation (PAA-RT). Different embodiments differ in the characteristics of the described components, but all share the illustrated steps.

FIG. 4: Alternative Reagents for Stepwise Peptide or Protein Degradation.

FIG. 6: Codon usage frequencies in humans, human mitochondria, mice, and E. coli.

FIG. 7: Illustration of the "Knob" embodiment of reverse translation (RT).

SUMMARY OF THE INVENTION

Figure 3:
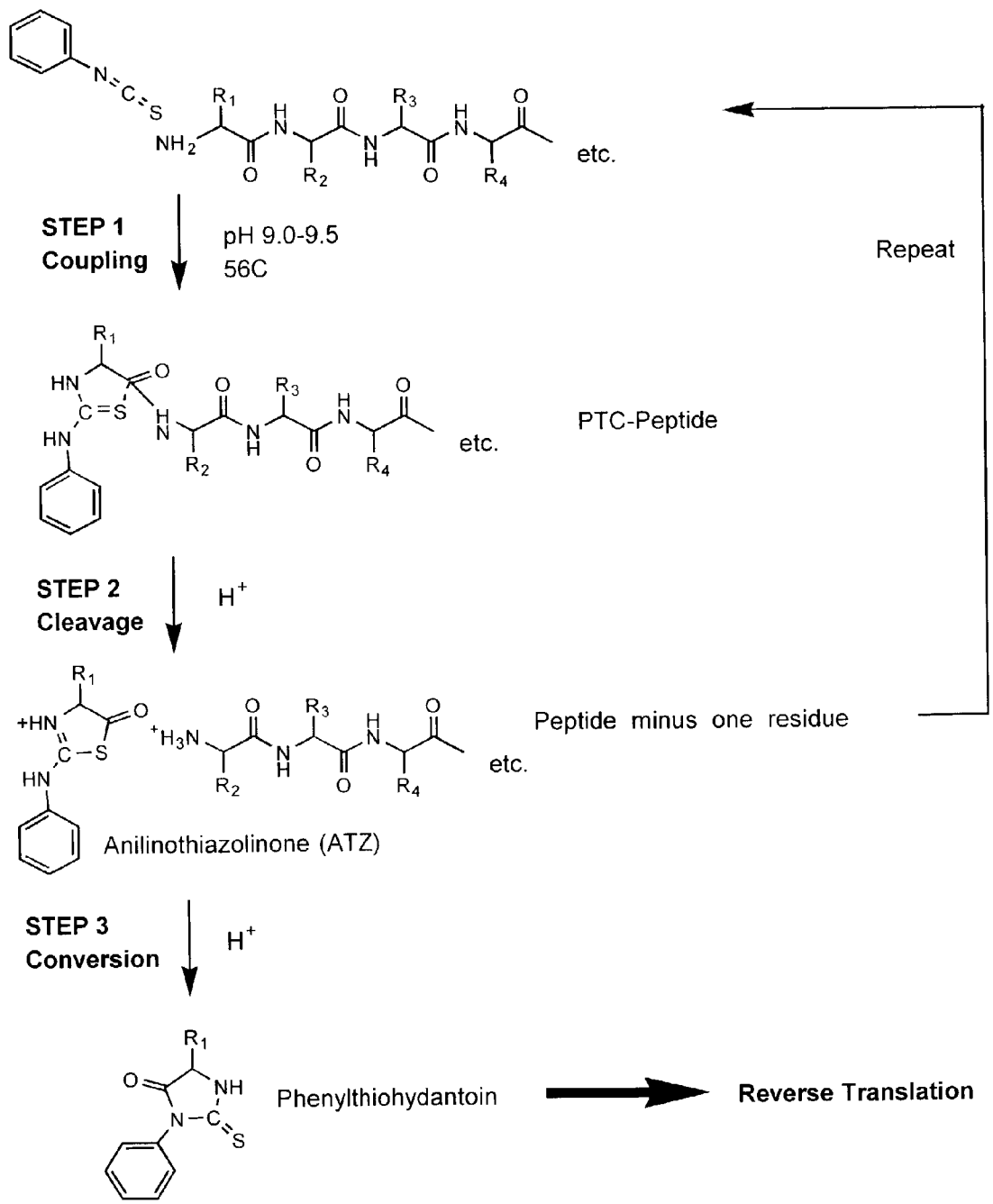
FIG. 3: Chemistry of Edman Degradation of polypeptides.

The invention describes methods and compositions of matter that enable poly-amino acid reverse translation (PAA-RT). PAA-RT is the process by which a poly-amino acid (PAA; a peptide or protein) is directly translated to form the corresponding encoding polynucleotide. The practical purpose of PAA-RT is to amplify the information encoded in the amino acid sequence of an unknown PAA. Amplification facilitates the determination of the PAA's identity, structure, and function.

PAA-RT involves a sequence of three steps, which are repeated one time for every amino acid to be reverse translated to its encoding codon. The steps of the PAA-RT cycle are;

1) PAA Terminal Amino Acid Degradation: A PAA of interest is degraded by Edman Degradation or similar chemical degradation reaction to release a single terminal (C- or N-terminal) amino acid derivative.

2) Reverse Translation (RT): RT is the central step in PAA-RT. RT is the appearance of an appropriate codon in response to its corresponding amino acid—in essence, the swapping of an amino acid for its encoding codon. RT involves novel methods and novel compositions of matter.

In RT, the cleaved amino acid derivative from Step 1) is exposed to a mixture containing Reverse Translation Elements (RTE) and a collection of various single codon derivatives. Collectively, the various codon derivatives encode the anticipated cleaved amino acids. A RTE is a molecule, particle, or surface capable of binding both the amino acid derivative and the encoding codon derivative. The purpose of the RTE is to enable the exchange in solution of an encoding codon derivative in response to the appearance of its corresponding amino acid derivative.

3) Polynucleotide Synthesis: The codon derivative obtained from Step 2) is reacted with a nascent polynucleotide chain to grow a peptide-encoding polynucleotide. Thus the PAA-encoding oligo/polynucleotide is assembled one codon at a time.

There are many practical uses for the produced oligo/polynucleotide, the corresponding gene, and the cloned/expressed PAA. These include, but are not limited to;

Detection of a miniscule amount of a known PAA (for example in a medical diagnostics setting), Discovery of a previously unknown PAA (for example in drug discovery or proteomics), and Amplification of a small amount of PAA (for structure/function research).

Other practical uses exist for peptides and proteins derived from the oligonucleotides obtained by PAA-RT. These uses are extremely widespread, because so many different types of proteins can be obtained by PAA-RT. Uses include but are not limited to biopharmaceutical, industrial, research, military defense, forensic, and diagnostic applications.

In detail, the invention concerns a method for isolating a codon comprising the steps:
(a) contacting an amino acid degradation product from a peptide or protein in a solution with a substrate to which the codon is attached,
(b) allowing specific complexation of the amino acid degradation product to the substrate,
(c) contacting the complex with a solid-phase capture material,
(d) washing to remove substrate that is not bound to the solid-phase capture material, and
(e) releasing the attached codon from solid-phase captured complex.

The invention additionally concerns the embodiment of such method further comprising a step of degrading the amino acid residue from a peptide or protein prior to step (a).

The invention additionally concerns the embodiment of such method wherein the amino acid degradation product is added to a solution containing the substrate.

The invention additionally concerns the embodiment of such methods wherein the substrate is added to a solution containing the amino acid degradation product.

The invention additionally concerns the embodiment of such methods wherein the substrate comprises a plurality of copies of codons.

The invention additionally concerns the embodiment of such methods wherein the substrate comprises a plurality of complexation sites for an amino acid degradation product.

The invention additionally concerns the embodiment of such methods wherein the amino acid degradation product is obtained from a carboxy- or amino-terminal amino acid of a peptide or protein.

The invention additionally concerns the embodiment of such methods wherein the degrading step is performed by Edman degradation of a peptide or protein.

The invention additionally concerns the embodiment of such methods wherein the solid phase capture material binds to the complex.

The invention additionally concerns the embodiment of such methods wherein the codon has been chemically modified for oligonucleotide synthesis.

The invention additionally concerns the embodiment of such methods wherein the substrate with attached codons have specific binding sites selected from the group consisting of antibody-derived molecules and molecularly-imprinted polymers.

The invention additionally concerns a method for isolating a codon comprising:
(a) contacting a solution containing a plurality of compounds that are conjugates of amino acid degradation products and their encoding codons with a plurality of solid phase substrates that contain binding sites that are specific for amino acid sidechains,
(b) allowing specific complexation of the conjugates to the solid phase substrates,
(c) contacting the complexes with a solution containing an amino acid degradation product from a peptide or protein,
(d) allowing the amino acid degradation product to displace conjugates from their specific binding sites on the solid phase substrate, and
(e) removing the solution containing the displaced conjugates.

The invention additionally concerns the embodiment of such method further comprising a step of degrading the amino acid residue from a peptide or protein prior to step (a).

The invention additionally concerns the embodiment of such methods wherein the amino acid degradation product is added to a solution containing the the complex.

The invention additionally concerns the embodiment of such methods wherein the substrate comprises a plurality of complexation sites for amino acid degradation products.

The invention additionally concerns the embodiment of such methods wherein the amino acid degradation product is obtained from a carboxy- or amino-terminal amino acid of a peptide or protein.

The invention additionally concerns the embodiment of such methods wherein the degrading step is performed by Edman degradation of a peptide or protein.

The invention additionally concerns the embodiment of such methods wherein the codon has been chemically modified for oligonucleotide synthesis.

The invention additionally concerns the embodiment of such methods wherein the substrate with attached codons have specific binding sites selected from the group consisting of antibody-derived molecules and molecularly-imprinted polymers.

The invention additionally concerns a method for isolating a codon comprising:
(a) forming a mixture of an amino acid degradation product from a peptide or protein and a plurality of conjugates of amino acid degradation products and their encoding codons,
(b) contacting the mixture with a plurality of solid phase substrates,
(c) allowing the amino acid degradation product and the conjugate to compete for specific binding sites on the solid phase substrate, and
(d) removing the solution phase containing non-bound conjugate and non-bound amino acid degradation product from solid phase substrate.

The invention additionally concerns the embodiment of such method further comprising a step of degrading the amino acid residue from a peptide or protein prior to step (a).

The invention additionally concerns the embodiment of such methods wherein the substrate comprises a plurality of complexation sites for amino acid degradation products.

The invention additionally concerns the embodiment of such methods wherein the amino acid degradation product is obtained from a carboxy- or amino-terminal amino acid of a peptide or protein.

The invention additionally concerns the embodiment of such methods wherein the degrading step is performed by Edman degradation of a peptide or protein.

The invention additionally concerns the embodiment of such methods wherein the codon has been chemically modified for oligonucleotide synthesis.

The invention additionally concerns the embodiment of such methods wherein the substrate has specific binding sites selected from the group consisting of antibody-derived molecules and molecularly-imprinted polymers.

The invention additionally concerns an isolated substrate that has one or more specific binding sites for an amino acid degradation product of a peptide or protein and has one or more codons attached thereto.

The invention additionally concerns the embodiment of such isolated substrate in which the binding sites are formed by antibody-derived molecules or molecularly imprinted polymers.

The invention additionally concerns the embodiment of such isolated substrate in which the codons are attached to the substrate via a cleavable linker.

The invention additionally concerns the embodiment of such isolated substrate in which the linker contains a moiety selected from the group consisting of an ester, an amide, an anhydride, and a disulfide.

The invention additionally concerns the embodiment of such isolated substrate in which the 3' nucleotide in the codon is labeled with a phosphoramidite group.

The invention additionally concerns the embodiment of such isolated substrate in which the codon has protecting groups for oligonucleotide synthesis methods.

The invention additionally concerns the embodiment of such isolated substrate in which the codons are attached to the substrate via noncovalent binding.

The invention additionally concerns an isolated organic compound comprising an amino acid degradation product of a peptide or protein conjugated to a codon that encodes the amino acid.

The invention additionally concerns the embodiment of such isolated organic compound wherein the isolated organic compound has a linker between the amino acid degradation product and the codon.

The invention additionally concerns the embodiment of such isolated organic compounds wherein the isolated organic compound has a cleavable linker between the amino acid degradation product and the codon.

The invention additionally concerns the embodiment of such isolated organic compounds wherein the isolated organic compound has a linker between the amino acid degradation product and the codon, the linker containing a moiety selected from the group consisting of an ester, an amide, an anhydride, and a disulfide.

The invention additionally concerns the embodiment of such isolated organic compounds wherein the isolated organic compound has a linker between the amino acid amino acid degradation product and the codon in which the the linker contains a moiety selected from the group consisting of an ester, an amide, an anhydride, and a disulfide.

The invention additionally concerns the embodiment of such isolated organic compounds wherein the isolated organic compound has protecting groups for oligonucleotide synthesis methods.

The invention additionally concerns the embodiment of such isolated organic compounds in which the amino acid degradation product is an Edman degradation product.

The invention additionally concerns the embodiment of such isolated organic compound which the 3' nucleotide in the codon is labeled with a phosphoramidite group.

Abbreviations and Definitions

Abbreviations (Some Are Defined Below):
AIBN, azobis-(isobutyronitrile); C-AA, conjugate of an amino acid (or derivative thereof) and a codon (or derivative thereof); EDGMA, ethylene glycol dimethacrylate; IMAC, immobilized metal affinity chromatography; Kd, dissociation constant; MAA, methacrylic acid; MIP, molecularly-imprinted polymer; mRNA, messenger ribonucleic acid; PAA, poly-amino acid; PAA-RT, poly-amino acid reverse translation; PITC, phenylisothiocyanate; RNA, ribonucleic acid; RT, reverse translation; RTE, reverse translation element; SCFv, single chain Fv fragment (single chain antibody); ssDNA, single-stranded DNA; 2-Vpy, 2-vinylpyridine.

Definitions:
Antibody-Derived Molecule: A peptide or protein that specifically binds to another molecule through a binding site whose overall three-dimensional structure and amino acid sequence originates from naturally occurring immunoglobulin variable regions. Antibody-derived molecules include but are not limited to whole IgG molecules, Fab fragments, and single chain antibodies.

Aqueous Solution: A liquid medium that is more than 50% water by volume.

Artificial Antibody (or Receptor): A molecule that has one or more binding sites that is complementary in shape and/or charge to another molecule. The artificial biomolecule specifically binds to the complementary molecule.

Chemical Reaction: The chemical transformation of one or more molecules (reactant(s)) to form one or more different molecules (product(s)).

Codon: A sequence of two or more chemically coupled nucleotides, which correspond to or "encode" an amino acid. The definition includes but is not limited to the conventional definition of codon in which three nucleotides are coupled to form the coding unit.

Informational Coupling: The act of translating a unit of biochemical information (information "A") into another, corresponding, unit of information (information "B"). Information is carried in the form of chemical structures—amino acids and nucleic acids—linked into polymers. The polymers have been termed "informational macromolecules" (Lehninger, 1975). The act of informational coupling is a physical process carried out by informational coupling molecules/organelles/materials. For example, a ribosome in concert with transfer RNA molecules carries out informational coupling of an mRNA to its corresponding protein.

Molecular Imprinting: A process whereby specific binding sites to a chosen target (imprint) molecule are introduced into synthetic materials. The binding material is usually an organic polymer. Typically, functional and cross-linking monomers are co-polymerized in the presence of the imprint molecule, which acts as a molecular template. Subsequent removal of the template molecule reveals binding sites that are complementary in shape and size to the imprint molecule. In this way, molecular memory is introduced into the polymer, enabling it to re-bind the imprint molecule with high specificity.

Organic Solution: A liquid medium that is more than 50% organic solvent by volume.

Poly-amino Acid (PAA): A natural linear polymer consisting of 2 or more amino acids coupled through peptide bonds. This definition encompasses peptides, polypeptides, and proteins.

Poly-amino Acid Reverse Translation (PAA-RT): A process whereby a polynucleotide is synthesized directly from the PAA that it encodes.

Print Molecule: A molecule to be molecularly imprinted, also known as a template molecule.

Reverse Translation (RT): Informational coupling of an amino acid into an encoding codon.

Reverse Translation Element (RTE): A molecule, molecular complex, or material that is the physical location of informational coupling in reverse translation and poly-amino acid reverse translation. RTEs have two functional characteristics. One characteristic is that they bind specific amino acids or amino acid derivatives. The second characteristic is that binding of the amino acid/amino acid derivative causes or facilitates an elevation in the solution phase concentration of a codon or codon derivative that encodes the bound amino acid.

DETAILED DESCRIPTION OF THE INVENTION

The Challenge: Is it Possible to Directly Couple the Reading of a Peptide or Protein Sequence to the Synthesis of its Encoding Oligo or Polynucleotide?

The key to reverse translation is the step of informational coupling of individual amino acids to their corresponding codons. Natural codons are trinucleotides. The three-nucleotide sequence of a codon specifies (encodes) a specific amino acid (FIG. 1)(Lehninger, 1975). There is no chemical structural resemblance of a codon with its encoding amino acid. In other words, it is not possible to visualize a chemical structural resemblance of a codon and its encoding amino acid. Conversely, one cannot look at the chemical structure of an amino acid and intuitively identify a corresponding encoding codon.

In nature, informational coupling during the translation of a nucleic acid into a peptide or protein (poly-amino acid, PAA) is carried in cells using tRNA and ribosomes. The biological apparatus that includes tRNA and ribosomes recognizes both the encoding codons and the appropriate corresponding amino acids, and enables the synthesis of the mRNA-encoded PAA. Thus, ribosomes and tRNA are the centers of informational coupling in natural translation.

As stated above, reverse translation (RT or PAA-RT (see definitions)) is not known to occur in nature. There is no reverse translation informational coupling counterpart to tRNA and ribosomes. Proteins, peptides, or even single amino acids are not known to be directly reverse translated to form RNA, DNA, or codons. Moreover, RT and PAA-RT have not been demonstrated by any man-made means.

Taking nature's solution of informational coupling into consideration, it would seem reasonable to suppose that reverse translation (RT or PAA-RT) would require informational coupling centers analogous to tRNA/ribosomes. Such centers of informational coupling are not known to exist in nature and, until the present invention, have not been conceived of by man.

The Solution: Informational Coupling and Reverse Translation

As described above, it is recognized that the key to inventing a method of reverse translation is to devise a means of "informational coupling" of amino acids and codons. The described invention accomplishes and discloses this and, for the first time, enables RT and PAA-RT. I will first describe the process in general terms, and then give details of the components of the process.

The process of poly-amino acid reverse translation (RT and in its more useful form, PAA-RT) is the direct chemicophysical informational coupling of a PAA to its encoding oligonucleotide sequence. In both forms, the key to the invention is the concept of the information transfer element, the so-called Reverse Translation Element (RTE). The RTE is a physical structure that can specifically associate with both an amino acid and its encoding codon and mediate the exchange of the amino acid for the codon, enabling reverse translation. By analogy with tRNA molecules, there are multiple RTE species, at least one for every type of amino acid to be reverse translated.

This can occur through one of several processes, such as competitive binding, displacement, or another process in which one molecule (amino acid-derived) is replaced with another (codon-derived).

The eluted codon derivative reacts with a nascent growing solid phase oligonucleotide. This step is based on conventional oligonucleotide synthesis methods.

The oligo (either ssDNA or RNA) can be used to hybridize with the cell-derived full-length coding gene (RNA or ssDNA). The hybridization product can then be amplified by PCR, or another nucleic acid amplification method (Ahern, 2001). The gene can be expressed according to standard methodologies to produce the encoded protein.

Single step reverse translation (RT) of an amino acid into its codon is described in enabling detail in this disclosure. However, the more complex embodiment, PAA-RT, is preferred to RT for its larger field of practical uses. PAA-RT is described in detail in the preferred embodiments. PAA-RT includes the cycling of three steps, one of which is RT. Each cycle causes the degradation of one amino acid from the PAA, reverse translation of one amino acid into its encoding codon, and addition of the codon to a growing oligo/polynucleotide chain. The process is cycled, as many times are is necessary to provide a polynucleotide of sufficient length. FIG. 2 shows one round of the cycling process. Some general discussion of each of the three steps is warranted. Each of the steps can be carried out in more than one way with the same result.

Perhaps the greatest utility value of the invention is that reverse translation permits molecular amplification of a PAA. This occurs by two mechanisms. One mechanism is that by converting the PAA to its encoding polynucleotide, its informational content of the PAA can be amplified via PCR or another nucleic acid amplification method. The second mechanism is that during the amino acid-for-codon exchange a small number of amino acid molecules (as few as one) is exchanged for many copies of codon molecules. For example, the application of one amino acid molecule results in the elution of many codon molecules during a round of reverse translation. Although not explicitly described in this disclosure, this second amplification mechanism can be used in a more direct exchange of a single copy of an amino acid for multiple copies of the same amino acid, rather than encoding codons. The PAA would then be directly amplified in direct amplification of individual amino acids which could be assembled to multiple copies of the original PAA by standard peptide synthesis methods.

Descriptive Summaries of Steps of PAA-RT:

(1) The first step is stepwise cleavage of individual amino acids from the PAA. Most commonly, this involves a chemical Edman degradation or other similar stepwise protein degradation (Bhown, 1987; Hancock, 1984; Findlay & Geisow, 1989). These are always terminal degradations, removing a single amino acid from one end of the peptide chain.

Both amino and carboxy terminal degradations are known, but amino terminal reactions are more commonly used. Terminal degradation reactions such as the Edman degradation are commonly used in protein chemistry for sequencing proteins and peptides. Automated instruments for carrying out this chemistry are commercially available and widely used.

Throughout this document, the degradation reaction described will be the Edman degradation, although the invention contemplates other similar C- and N-terminal degradation reactions. Edman degradation uses the reagent phenylisothiocyanate (PITC) (FIG. 3). Other N-terminal degradation reactions include the use of alternative reagents including fluorescein isothionate (FITC), 4-nitrophenyl-isothiocyanate, 311-PTH (4-[3-pyridyinylmethylaminocarboxypropyl]phenylisothiocyanate), 4-N,N-dimethylaminoazobenzene-4'-phenylisothiocyanate (DABITC), S-(thiobenzoyl)thioglycolic acid (Bhown, 1987; Shively, 2000; Findlay & Geisow, 1989). Some of these are illustrated in FIG. 4. Carboxy terminal degradation reactions include, but are not limited to, formation of hydrazide, oxazole, cyanamide, oxazolidone, acyl urea, and thiohydantoin derivatives (Bhown, 1987; Inglis, 1991; Dupont et al., 2000).

C- and N-terminal enzymatic degradation reactions are also possible (Bhown, 1987).

Figure 5:
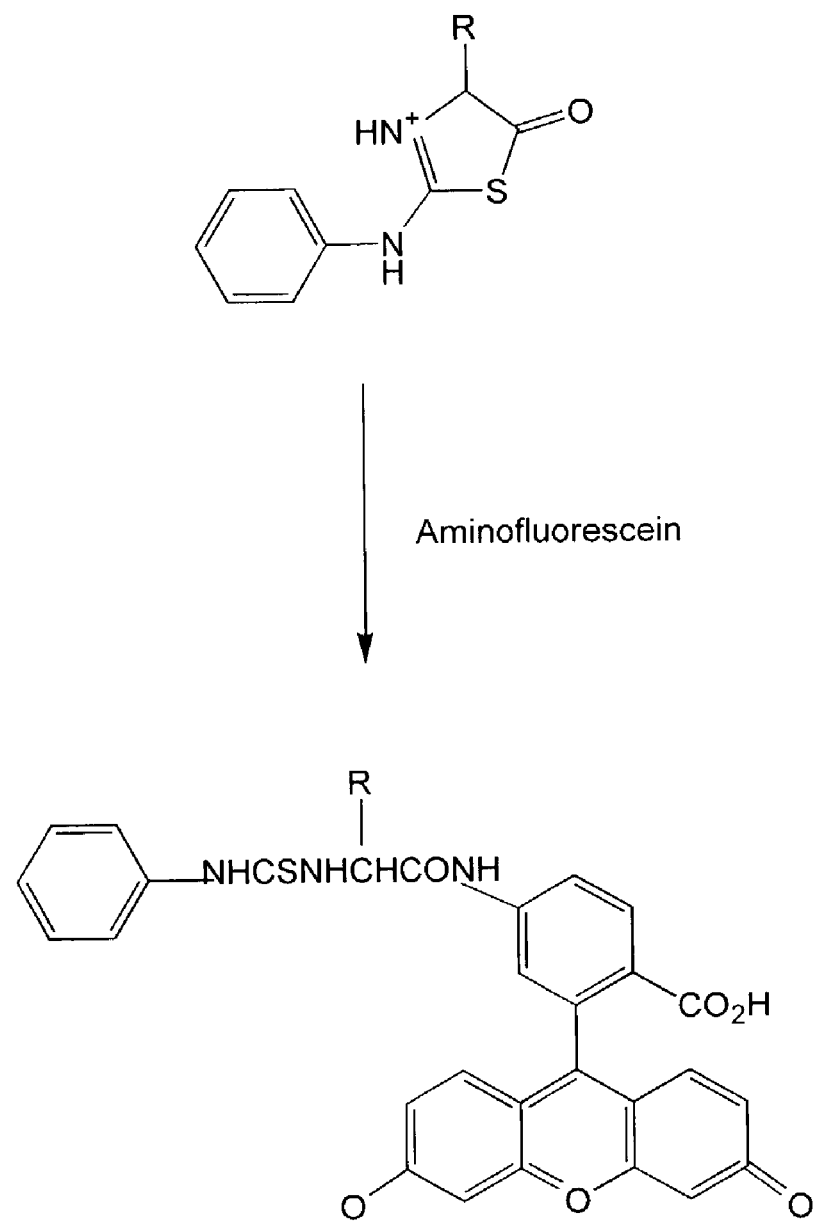
FIG. 5: Formation of aminofluorescein derivatives of Edman degradation products. The amino acid sidechains are designated by R (Shively, 2000).

In addition to using alternative degradation reagents, intermediates known as anilinothiazolinone (ATZ) amino acids, which occur during Edman degradation, have been chemically modified (see FIG. 3). For example, the AZT derivatives can be reacted with aminofluorescein to give fluorescein phenylthiocarbamide (PTCAF) derivatives (FIG. 5). This or other post-Edman chemical modifications can be used in the process of RT as well. Corresponding procedural changes to the process of RT would be relatively minor for one skilled in the art.

Degradation reactions are performed in various formats including solution phase, solid phase, and on chips (Brown, 1987, Wurzel & Wittmann-Liebold, 2000). Any format used will be acceptable as long as the amino acid derivative is formed in a way that can be usable.

In the case of large proteins, the entire protein does not have to be reverse translated, but the longer the sequence, the more likely it will be that reverse translation will yield a unique amino acid sequence, allowing definitive identification of the protein. Amino acid sequences of 10 are almost always unique and sufficient to identify proteins (see below). In the case of proteins, the segment of peptide to be subjected to degradation should be 5–7 amino acids in length or longer.

During stepwise degradation of a peptide, the released amino acid is chemically modified. For example in Edman degradation, a PTH derivative is formed (FIG. 3). Other types of degradation yield other types of chemical products, but in all cases they are products that are retain structural characteristics of the original amino acid sidechain.

(2) This step is RT (reverse translation according to the definitions, above). The released amino acid derivative is added to a mixture of RTE's and codon derivatives. Addition of the amino acid derivative to the mixture results in the elevation of the concentration of unbound codon derivative. This can occur through one of several processes, such as competitive binding, displacement, or another process in which one ligand (amino acid-derived) is replaced with another (codon-derived). The concept, preparation, and use of RTEs represents the key component of the present invention and will be described in detail below.

(3) The eluted codon derivative reacts with a growing solid phase nascent oligonucleotide. This step is based on conventional oligonucleotide synthesis methods. The features of the codon derivative that are unique to RT are cleaved. The codon derivative is added to the nascent encoding oligonucleotide. The oligo is preferably synthesized on a conventional support, such as controlled pore glass (CPG) beads. The codons are added to the growing oligonucleotide chain, either directly on the support, via an organic tether, or via an intervening known oligo, such as a primer sequence.

General Comments:

Steps 1–3 are repeated. Each cycle translates one amino acid into its encoding codon. The number of cycles performed will depend on various factors including the length of the PAA, any chemical modification of the PAA, and peptide lengths resulting from partial digestion of the PAA.

Complementary Methods, Known in the Art

Other technical procedures, known in the art, will commonly be used in conjunction with the invention. For example, preceding reverse translation, the protein or peptide of interest will be purified and may also be partially digested to create smaller peptide fragments to be reverse translated. Following reverse translation, the polynucleotide may be amplified by PCR, in vitro translation or another amplification method. It may be cloned to enable expression of the reverse translated protein. Further downstream steps will include protein identification by mass spectroscopy, peptide mapping, sequencing or other method. The biological activity of the ensuing protein will commonly be tested. These other steps are common laboratory procedures well known to trained scientists.

Some of the more common peripheral procedures are described here in greater detail;

Methods Performed Prior to RT

PAA Isolation: A substantially purified PAA is required for reverse translation. The PAA can be purified by conventional means well known in the art (Dennison, 1999; Hancock, 1984). PAA purification need not be absolute, but must be sufficient for reverse translation to result in a single dominant oligonucleotide of the correct sequence.

One means of purification that may often be used is two-dimensional electrophoresis (Link, A., 1999; Hames, 1998; Rabilloud, T., 2000). This method is commonly used in the fields of biochemistry and proteomics to separate the proteins on a gel. The protein of interest can be extracted from an area on the gel. Protein extraction can be performed manually or by using an automated spot picker (Gevaert et al., 2000). Alternatively, the protein may be transferred from the gel to a membrane by a typical Western blot procedure.

Another means of purification is by capture by a specific binding interaction, a method generally known as affinity purification (Hermanson et al., 1992). For example, a solid-phase antibody or receptor might is used to specifically capture one unknown protein from a mixture of many unknown proteins. Affinity purification is useful in, for example, looking for proteins which bind to a given antibody, receptor, ligand (or other small molecule), DNA sequence, or drug. Captured protein is eluted by reasonable methods, including protein denaturation methods, and the protein is subjected to RT.

PAA Partial Digestion: Often, the purified PAA is reverse-translated without being partially digested. However, in many cases, the naturally occurring terminal amino acid of the full-length PAA is not amenable to stepwise C- or N-terminal degradation (for example, by Edman degradation). The terminal amino acid may be may be blocked by post-translational modification, for example by acetylation (Wold, 1981). Also, amino acids that are not terminal, but are near the terminus may also be hinder stepwise degradation. When post-translational modification is likely to interfere with Edman (or other degradation reaction), the PAA will be partially digested prior to RT. Because the nature and identity of the PAA will be initially unknown, the decision to perform partial digestion will depend on various factors, including likelihood of terminal post-translational modification, amount of PAA available, and surmised size of the PAA.

Partial digestion is a common practice in protein chemistry (Heilman, 2000; Quadroni & James, 1999). It can be carried out in various formats including in solution, in a gel (e.g., polyacrylamide), on a membrane (e.g., polyvinylidine difluoride, PVDF), and in a microfluidics chip (Hellman, 2000; Quadroni & James, 1999; Wang et al., 2000; Lahm & Langen, 2000). The digestion reaction is most commonly either carried out using a cleaving chemical or an enzyme (Quadroni & James, 1999). Chemical methods include the use of cyanogen bromide (cleavage at methionine residues), 2-nitro-5-thiocyano-benzoic acid ("NTB", cysteine cleavage), (2-(2-nitrophenylsulfenyl)-3-methyl-3-bromoindolenine) ("BNPS-skatole", tryptophan cleavage), hydroxylamine (Asn-Gly bonds), and acid (Asp-Pro bonds) (Quadroni & James, 1999). Alternatively, a number of proteolytic enzymes can be used which are commercially available in "sequence grades" of purity (e.g., Sigma Chemical Co., St. Louis, Mo.). Because hydrolytic enzymes are sequence-specific in their targets, enzymatic digestion results in a series of distinct peptide products. For example, the enzyme trypsin is often used. Trypsin is an endoprotease, which cleaves specifically on the C-terminal side of positively charged amino acids (lysine and arginine). Assuming that a typical protein is made of 5% arginine and 5% lysine residues, and is about 50 kDa in size (approx. 440 amino acids), trypsin digestion would yield approximately 45 peptides of an average length of 10 amino acids. The use of another protease, LysC, generates longer fragments than trypsin because it preferentially cleaves at only lysine residues (Hellman, 2000).

The step of fragmentation is not always required. If the terminus to be degraded is not terminally blocked (for example, N-acetylated), then the N- (or O-) terminus can be directly subjected to sequential reverse translation. If the terminus is blocked, or amino acids near the N- (or O-) terminus are post-translationally modified, the terminal sequence is amenable to reverse translation. In those cases, the PAA is partially fragmented to form short peptides, one or more of which could be subjected to RT. Generally speaking, if a PAA would be subjected to partial fragmentation for conventional amino acid sequencing, it will be partially fragmented for RT. The methods of partial fragmentation of PAAs are well known in the literature of protein sequencing.

PAA Fragment Purification: Following digestion, the generated peptides are separated by HPLC, capillary electrophoresis, or some other conventional means. These are the same methods used in purifying peptides for Edman degradation in conventional sequencing. Here, instead of Edman degradation, one or more of the purified peptide fragments is subjected to reverse translation. Purification of digested protein fragments is a well-known art (Brown, 1987). Purification options include HPLC and capillary electrophoresis.

Peptides may also be concentrated if advantageous. A number of common methods exist for this task (e.g., Gevaert et al., 2000).

Automated Edman degradation (or similar terminal degradations) is routinely used for direct peptide sequencing. In those cases, PAAs to be sequenced are prepared at no lower than slightly sub-picomole amounts (as opposed to femtomole or attomole amounts). The reason for the peptide mass limit is that such levels are required for direct detection of the sequenced amino acids (Hellman, 2000). In the case of reverse translation, lower amounts of peptides are feasible, because the degraded amino acids will not be directly detected. Only after the encoding polynucleotide is formed (amplification), will detection occur. If extremely low concentrations of peptides are to be purified, they may not be detectable by conventional means such as far-UV detection. In such cases, fractions may be collected and individual fractions corresponding reasonably to elution volumes of peptides will be subjected to RT. A successful RT series will indicate that a single peptide was in a chosen fraction.

Methods Performed After RT

There are a number of directions that one can go with a newly synthesized oligo/polynucleotide. One thing that can be done is direct detection via hybridization to labeled ssDNA or mRNA. Detection of the label can be carried out by fluorescence, luminescence, visible or UV absorbance, radioactivity, etc. Direct detection is especially attractive in RT methods where amplification is built into the amino acid-for-codon swapping step (see below, for example in the "Knob" variation). In those methods, a single copy of PAA results in the synthesis of multiple copies of oligonucleotide.

Alternatively, the oligo can be used to capture a complementary ssDNA or mRNA encoding a full length or nearly full-length gene for the PAA. The captured gene can be amplified by polymerase chain reaction (PCR) or another similar amplification reaction (Ahern, 2001). The gene can then be directly identified or cloned into one of many available vectors and the protein can be expressed in vivo or in vitro (Sambrook et al., 2001). Cloning and expressing a gene or gene fragment from an oligonucleotide such as is produced by RT is common practice in molecular biology and established methods are widely known (Sambrook et al., 2001).

Another amplification strategy is to amplify the reverse translated oligonucleotide before capturing the gene that it encodes. In this case, the reverse translated oligo would generally be flanked on one or both ends by known sequence primers (Ahern, 2001). One primer could be on the synthetic support in advance of RT and the reverse translated codons could be added to this primer as RT proceeds.

The Relevance of Genetic Code Degeneracy

In nature, the genetic code is degenerate, meaning that there is often more than one codon that encodes a single amino acid (Avers, 1976). There are Four DNA nucleotide building blocks (A, T, G, and C) which can be combined in 64 ways to make trinucleotide codons ($4^3$=64). Since there are 20 amino acids that are encoded, many amino acids have multiple corresponding codons (FIG.). For example, for the tripeptide, Ser-Met-Phe, the following codons are possible;
TCG
TCC
TCA TTT
TCT ATG TTC
Ser Met Phe This example illustrates a three amino acid sequence where Serine has 4 codons, Methionine has 1 codon, and Phenylalanine has 2 codons implying that Ser-Met-Phe can be coded by 4×1×2=8 sequences.

Because of the degeneracy, if one is presented with a gene, it is fairly straightforward to determine the encoded PAA. However, in the reverse situation, when one is given a PAA sequence, although it is easy to determine a sequence of codons that encodes the PAA, it is not apparent which codons are used to encode the PAA in nature.

Because most amino acids have multiple encoding codons (FIG. 1), assembly of an encoding oligo by reverse translation may not involve the codon used in the naturally occurring gene. For example, there are four codons that encode the amino acid alanine. The gene for a given protein uses only one of these to encode for an alanine residue at a given position in a PAA. If all four alanine codons were used with the same frequency in nature and if the RT codon is picked at random, there would be only a 25% chance that the natural codon will be inserted into the growing oligo during RT. As a PAA is reverse translated, each new codon that is added to the growing oligo will bring with it uncertainty whether that is the natural codon.

Thus, even though it will encode the desired PAA, an oligo that is synthesized through RT is likely not to have the same nucleotide sequence as the native gene. If the oligo is expressed, it will generate the correct PAA. However, comparison of the oligo sequence generated by RT will most likely differ from the natural gene sequence. This could have consequences, especially in hybridization of the RT-synthesized oligo to gene libraries (ESTs or full length genes).

Despite these apparent drawbacks, there are four important things that mitigate or obviate the issue of degeneracy:

1) Codons have a "wobble" base (Avers, 1976). As can be seen in FIG. 1, the first two codons are usually the same for a given amino acid, and variability comes in the third codon. It is believed that the early genetic code only used two bases, such that today the third base is not used in determining the encoded amino acid. The third nucleotide, the so-called "wobble" nucleotide is often irrelevant in that in many cases, the first and second codons determine the amino acid.

The existence of a wobble base is the reason why there are fewer transfer RNAs than there are codons in nature. Transfer RNAs tend to be able to "ignore" the wobble base so that multiple codons for the same amino acid are recognized by a single tRNA. Intriguingly, this convenience of nature also becomes a convenience of (manmade) reverse translation.

2) There are methods of hybridizing polynucleotides in which the stringency of matching is intentionally lowered (Sambrook et al., 1989). For example, hybridization can occur in tetramethylammonium chloride (TMAC)(Honore & Madsen, 1997). Sequences that are similar but not exact will hybridize using this reagent.

3) Codon usage is not random. As shown in FIG. 6, certain codons are used more than others for encoding a given amino acid (GENbank data, National Institutes of Health, Bethesda, Md.). The usage patterns are not universal, but show species to species variation. Indeed, codon usage varies within humans in that the mitochondrion, which is genetically distinct, is different from human cellular usage.

4) Codons can be used containing so-called degenerate bases (Agrawal, 1994). Among these is the use of hypoxanthine I as a base that can be inserted into positions of degeneracy. Others are known as well (Agrawal, 1994). These compounds can also be used in hybridization probes, sequencing primers, and PCR primers.

Thus, although the genetic code is degenerate, there are at least four reasons why reverse translation can be carried out and the resulting oligonucleotide can hybridize to the full-length gene, even if the nucleotide sequence of the reverse translated oligo and the corresponding gene segment vary somewhat in sequence. In RT, one would use codons that are statistically most likely to encode the amino acid in nature. The resultant oligo will encode the PAA segment that has been reverse translated. In addition, thanks to the wobble in the third position and the use of stringency-lowering reagents such as TMAC, the formed oligo will hybridize to the naturally encoding gene, even if the base sequence varies.

How Many Amino Acids Must be Reverse Translated to Identify the PAA?

RT can be performed on small peptides, in which case the entire peptide is reverse translated to an encoding oligonucleotide. However, in many cases RT will be performed on proteins that will be impractical to entirely reverse translate, because of a very long sequence, or because of intermittent post-translational modifications. In these cases, RT is performed on a subset PAA to generate an oligonucleotide that encodes a short internal or terminal peptide sequence. For example, a protein to be reverse translated might have a total of 300 amino acids in its sequence. Only a small peptide sequence, consisting of, say 7 amino acids, may be reverse translated. The resulting encoding oligonucleotide will be used to obtain the full-length gene using standard molecular biology protocols.

To obtain the correct protein during cloning, the oligo generated during RT must be unique to that protein. For this reason, the number of amino acids to be RT must be a certain size to ensure uniqueness. (For example, although a particular dipeptide may well be found in many different natural proteins, a specific decapeptide sequence may be found in only one protein in nature.) As shown in the calculations below, there is no defined number of amino acids that can be considered a "fingerprint" of uniqueness, but rather the probability of uniqueness rises substantially with length of the peptide sequence.

Calculations: Probability of a Unique Amino Acid Sequence.

Number of sequences possible in a peptide to be reverse translated: $20^n$ (n=number of peptide amino acids. This number is less than or equal to the number of amino acids in the PAA.)

Number of peptides of length n within a PAA (for example, for tripeptides; amino acids numbered 1–3, 2–4, 3–5, etc.): $[M-(n-1)]$ (M=number of amino acids in a PAA)

Fraction of all possible peptide sequences of length n represented in a PAA of length M:

$[M-(n-1)]/20^n$

Random chance of a peptide of length n appearing in both PAA #1 and in PAA #2. Both PAA's being the same length, M:

The number of possible peptide permutations, $20^n$, can be considered analogous to the number of possible winning numbers in a lottery. The number of peptides that actually appear in one PAA can be considered analogous to the lottery numbers that are pulled from a hat, the "winning numbers". A reverse translated peptide from a second PAA can be considered analogous to a random lottery ticket that one has chosen. Thus, the chances of a peptide in PAA #2 being the same as a peptide in PAA #1 are governed by the same probability calculations as in a lottery;

Probability of Identity=$[M-(n-1)]/20^n$

We can now see what the random chance of a peptide coincidentally being the same as that found in a random protein. For the sake of example, assume we have performed RT on a peptide and we will look at the odds of that peptide matching a peptide of the same length in a random protein—a typical protein of 300 amino acids. The mean length of proteins has been estimated to be about 300 amino acids (White, 1992). By plugging in to the above equations, we can see that the probability of identity of two peptides within the two PAAs drops rapidly with peptide length.

For tripeptides, $$[M-(n-1)] = [300-(3-1)] = 298$$

$$20^n = 20^3 = 8000$$

Probability of identity = 298/8000 = 0.0373

This means that, on average, a tripeptide of a given sequence occurs in about 3.7% of all proteins.

Use of the same calculation shows that the odds of coincidental matching drops off rapidly:

| Number of amino acids in a peptide | Chance of that peptide occurring in a 350 amino acid protein |
|---|---|
| 3 | 0.0373 (3.73%) |
| 4 | 0.0019 (0.19%) |
| 5 | 0.00010 (0.010%) |
| 6 | 0.0000046 (0.00046%) |
| 7 | 0.00000023 (0.000023%) |

This Table shows that, if all sequences are random, the odds of a reverse translated short peptide occurring in another protein are quite small. (The size of the human proteome is estimated to be around $3 \times 10^5$ (Salzberg et al., 2001; Venter et al., 2001; International Human Genome Sequencing Consortium, 2001). Thus, if all proteins were random sequences, it would be sufficient to reverse translate as small as a 6–7 amino acid peptide to know with relative certainty that the oligo would uniquely match a single protein gene.

However, proteins are not random sequences, but often have homologous sequences. Homology usually arises from evolutionary forces. A protein may evolve to others (divergent evolution), or dissimilar proteins may evolve to a shared function (convergent evolution). One example involves tripeptides that comprise common motifs in proteins (for example, serving as a "binding handle").

In conclusion, the length of the reverse translated peptide required to give an oligonucleotide that is a unique fingerprint of that PAA depends largely on probability. If a random sequence is chosen, presumably by chance, then only 6–7 amino acids will need to be reverse translated to give a unique oligo. However, if a peptide is chosen that is highly homologous to other PAAs, then the sequence will have to be longer. The length will depend on the degree of homology but will rarely be longer than 12–15 amino acids.

DETAILED DESCRIPTION OF THE PREFERRED EMBODIMENTS

Three major embodiments of RT are described here, the so-called "Knob", "Displacement", and "Competitive" variations. In every case, a PAA terminal-chemical degradation step precedes a step in which an RTE is used to swap an amino acid derivative for a codon derivative. The codon derivative is covalently coupled to the growing encoding polynucleotide chain.

Above, I briefly listed steps required to carry out PAA-RT. In this section, I describe the specific details of RT—the central step in PAA-RT. The different embodiments accomplish the same end, reverse translation.

Reverse Translation: The "Knob" Variation

The Knob variation (FIG. 7) of RT involves "knob-type" RTEs. RTEs are prepared prior to performing RT. An RTE is analogous to a transfer RNA in that they are the physical entities at which amino acid/codon information transfer occurs.

Because there are 20 genetic code-encoded amino acids, to have a full complement of RTEs would require 20 unique RTEs. Since the genetic code is degenerate, there are 61 amino acid-encoding codons in the natural genetic code. Hence, there could be as many as 61 different RTEs. However, because of the various factors described above which obviate the need for a unique RTE for each codon, the number of unique RTEs will be closer to 20 than to 61 (see above discussion of degeneracy).

One option in Knob RT is to have RTEs with more than one species of codon attached to them, but all attached codons would encode the same amino acid. For example, a serine RTE could have all four different serine codons (FIG. 1) attached.

In the knob variation of RT, each RTE has two critical characteristics. First, it has one or more copies of a specific binding site that recognizes a specific amino acid sidechain. Second, each RTE has attached to it one or more copies of the encoding codons. The attached codon derivatives are attached in a way such that they can be released into solution. Attachment can be either covalent (for example, by an ester-, anhydride-, disulfide-, amide-, or carbonate-containing linker) or non-covalent (a specific binding site for the codon derivative).

The RTE can be made from any material or molecule that fulfills the main two requirements. Preferably, RTEs are made from either antibody-derived molecules or molecularly imprinted polymers (MIPs). Antibody-derived molecules include IgG, Fab, single chain Fv fragments, or any other antibody-derived construct. MIPs include various types of polymers including highly cross-linked acrylates and similar commonly used MIP polymers. The RTE can be the size of a macromolecule or small (sub-millimeter) particle.

Similarly, the specific capture surface can be made from either antibody-derived molecules attached to a common solid phase or from MIPs. The solid phase surface may be any shape, for example, planar or spherical particulate.

The Process of Knob-Type RT

The basic steps for the Knob variation of RT are described in this section.

In Knob RT, RTEs are used as follows:

(1) A cleaved (by Edman or other degradation) terminal amino acid derivative is mixed with a plurality of knob RTEs in aqueous or organic solution. If the RTE is made from protein, such as antibody, the solution will preferably be near neutral pH and aqueous. If the RTE is made from a MIP, the solution may be either aqueous or organic.

(2) The amino acid derivative is allowed to bind to the appropriate recognizing RTE. The amino acid sidechain (and also the possible surrounding structure) binds specifically to the RTE. Binding is preferably non-covalent, with affinities (dissociation constant, $K_D$) that are micromolar, nanomolar, or lower.

(3) The RTE-bound amino acid derivative is captured on a surface, which recognizes the derivatized portion of the amino acid derivative. This can be the Edman PTH group for example. It can also be a fluorescein group or other group as described above. In any case, the capture surface binds the derivatized portion of the cleaved amino acid that is common to all degraded amino acids. The non-bound RTEs are washed away. Alternatively, the amino acid derivative can be captured on the derivative-binding surface first, and then the RTEs can be introduced. In this case, the RTE binds to the amino acid sidechain extending from the capture surface. In any format, only the RTE bearing the appropriate amino acid derivative and corresponding codon is specifically captured. All others RTEs are washed away.

(4) The codons are then released from the captured RTE. By this point, incorrect RTEs are washed away leaving only RTEs with codons that correspond to the correct amino acid. The codons are released from the RTE by means (pH, salt, enzymatic cleavage, etc.) depending on the type of coupling. For example, a non-covalently bound codon could be released by high salt or small pH changes, and a carbonate or anhydride linked codon could be released by acid.

(5) The released codon is added to the growing encoding oligonucleotide by conventional oligonucleotide synthesis methods.

Greater detail is provided below for some of the steps and components mentioned above.

(1) Preparation of RTEs

RTEs in the knob variation can be made of any molecule, collection of molecules, or material that can; 1) go into suspension of solution, 2) can non-covalently and specifically bind one or more copies of a specific cleaved amino acid derivative, and 3) can covalently or non-covalently bind one or more copies of the corresponding codon. This is shown schematically in FIG. 7. Although I do not restrict the invention to certain types of molecules or materials to be used as RTEs, two types that are particularly attractive are antibody-derived molecules and molecularly imprinted polymers. Other types of molecules and materials that can be used as RTEs, but which will not be described in detail, include non-antibody proteins, dendrimers, zeolites and other cage molecules, and protein/polymer composites, such as antibody-coated beads.

Molecular imprinting (or template polymerization) is a well-established area of science (Haupt & Mosbach, 2000; Ngo, 1993; Wulff, 1998; Shea, 1994). In molecular imprinting monomers are polymerized in the presence of a non-polymerizing "print molecule". The polymer wholly or partially surrounds the print molecule in such a way that there is substantial shape and electronic complementarity between the polymer and the print molecule, much like the natural fit between an antibody and antigen. Research in the area has been ongoing for many years in many laboratories and numerous methods are widely known.

Molecularly imprinted polymers (MIPs) can be made from a variety of polymerizable materials including acrylics (Kempe & Mosbach, 1995; Odian, 1991), titanium oxide (Lee et al., 1998), silica (Katz & Davis, 2000), saccharides (Shi et al., 1999), self-organizing monolayers (Mallik et al., 1994), and proteins (Braco et al., 1990).

To my knowledge, no molecularly imprinted polymers have ever been prepared which have the essential characteristics of RTEs, described above. However, many reports have been published which substantiate each component of RTEs. Reports of each component of RTEs are described briefly here;

1) RTEs specifically and non-covalently bind amino acid derivatives from Edman (or other) degradation reaction. Very many publications have described molecular imprinting of amino acids and amino acid derivatives (O'Shannessy et al., 1989a; O'Shannessy et al., 1989b; O'Shannessy et al., 1989c; Andersson et al., 1990a; Andersson et al., 1990b; Kempe et al., 1993; Kempe & Mosbach, 1995). These reports have convincingly demonstrated that molecularly imprinted polymers (MIPS) can distinguish between even amino acids that are very similar in structure (glutamate vs. aspartate) and between D- and L-isomers of amino acids. Moreover, aromatic hydantoins (nearly identical in structure to the derivative group in Edman degradation) have been successfully used as template molecules in imprinting (Zhou et al., 1999; Zhou et al., 1999a).

2) RTEs covalently or non-covalently bind codon derivatives. A number of publications have shown that MIPs can be made to non-covalently bind nucleotides, nucleosides, and bases (Yoshikawa et al, 2001; Spivak et al., 1997; Spivak & Shea, 1998; Mathew & Buchardt, 1995; Mathew-Krotz & Shea, 1995; Shea et al., 1993). In addition, boronate-containing MIPs can bind vicinal hydroxyl groups in sugars such as those in ribose residues in RNA (Miyahara & Kurihara, 2000). Boronate-sugar linkages are covalent but highly reversible.

Molecules of various types can also be covalently attached to the surfaces of MIPs (Ye et al., 2001; Miyahara & Kurihara, 2000; Ray & Gupta, 1997; Kirsch et al., 2000; Ohkubo et al., 1994; Dhal et al., 1995). MIPs are made from a multitude of different monomers, most of which have high surface densities of some kind of functional group, such as a carboxyl group (for example, polyacrylates and polymethacrylates). These functional groups can be modified by covalent attachment following polymerization. During chemical modification, the specific binding pockets in the polymer can be protected ("blocked") by bound template molecule. Methods for conjugating molecules-to-molecules or molecules-to-particles are well known (Means & Feeney, 1971; Wong, 1991; Hermanson, 1996).

3) RTEs are soluble or suspended macromolecules, macromolecular assemblies, or particles. There is no restriction on their size as long as they are functional (i.e., they can be captured on a surface via specific binding interactions). MIPs have been shown to function in a wide range of formats including molecule-sized, irregular particles of all sizes, beads, membranes, and essentially planar surfaces (Yan & Kapua, 2001; Ye et al., 1999; Ye et al., 2001; Mallik et al. 1994; Kempe & Mosbach, 1995, Lee et al., 1998; Shi et al, 1998). Polymerization can occur with the intention of forming a shape or size of polymer.

The second main type of RTE is antibody-based. Antibody-derived molecules (see definitions above) are used to bind to the PAA degradation products. The antibody-based RTEs recognize cleaved amino acids with distinctive specificity. Antibody-derived molecules can be made by many methods including hybridoma and phage display technologies (Paul, 1995; Harlow & Lane, 1988). Scientists skilled in the art can generate antibody-derived binding sites that bind and distinguish between the various Edman (or other degradation reaction) products. Antibodies are known to have exquisite binding specificity and are able to discriminate between small antigenic structural differences.

The antibody-derived RTEs can consist of various structures. As stated above for MIP-based RTEs, the antibody-derived RTEs can have any format as long as it fulfills the three listed criteria. For example, the antibody-derived RTE can have one or more binding sites for amino acid derivatives and one or more binding sites for encoding codon derivatives. (They can be made from two different antibodies with different specificities.) Alternatively, the anti-amino acid antibody can be the only macromolecule in the RTE. In this case, the antibody RTE is labeled with codon derivatives. The codon derivatives are coupled to antibody sidechains (e.g. lysines or carboxylic acids). The codon-antibody linkage is cleavable by mild conditions (dilute NaOH for example). Small molecule-protein conjugates are well-established science (Means & Feeney, 1971; Wong, 1991; Hermanson, 1996). Yet another alternative is that antibody-based RTEs can consist of antibody-derived molecules coupled to beads or particles. Protein-coated beads are well known and used in various analytical methods. The beads are generally polymer-based and porous or non-porous. In the case of antibody-coated bead RTEs, the codons can be attached to or entrapped with the bead. The codons can also be attached to the antibody-derived molecule as discussed above.

(2) Preparation of Specific Capture Surface

The capture surface in knob-type RT is used to capture RTEs (FIG. 7) via binding to the Edman (or other) degradation product derivative group. As with the RTE, the two most attractive sources of binding functionality are MIPs and antibody-derived molecules. The capture surface differs from the RTE in its requisite criteria. The capture surface has the following essential criteria;

1) It must bind the Edman (or other) degradation product derivative. It must do so regardless of the amino acid, which has been cleaved. In this way the binding sites are specific for the derivative group, but non-specific for the sidechain of the amino acid.

2) It is preferably a solid. The capture surface captures the RTEs, which are mobile in either in solution or suspension. Once the correct RTE has been bound to the capture surface via the Edman product, the remaining "incorrect" RTEs are washed away from the capture surface.

The solid capture surface can be any shape including but not limited to particles (as in a column packing) or essentially a plane. One attractive form of capture surface is a molecularly imprinted polymer. This can take many solid forms as described above. The MIP is prepared to bind the PAA cleavage derivative portion of the amino acid. A second attractive form of capture surface consists of an antibody-derived molecule adsorbed, covalently linked, or otherwise coupled to a bead, particle, or surface. Antibody, or protein, coupling to solid surfaces is well known in the art (Means & Feeney, 1971; Wong, 1991; Hermanson, 1996). If the capture surface is in suspension (particles), then the capture particles it must be captured by, for example, filtration or magnetism.

(3) Preparation of Codon Derivatives

Chemical derivatives of codons are used in RT. In the Knob variation, the codon derivatives are either covalently or non-covalently bound to the surface of the RTEs. In contrast, in Displacement and Competitive RT, the codon derivatives are covalently conjugated to amino acid derivatives. (Both Displacement and Competitive RT use amino acid-codon derivative conjugates.)

Numerous chemically distinct codon derivatives can be used in the three described RT variations. Bioconjugate chemistry and oligonucleotide synthesis chemistry are very flexible branches of chemistry, and there are many ways to create compounds that fulfill the required criteria described below. One skilled in the art would be able to carry out the chemistry described here, and related known chemistry, to accomplish the necessary features.

In the invention, the preferred codon length is three nucleotides, the same as in nature. Derivatization can occur on any nucleophilic or electrophilic group on the codon. Typical and preferred derivatizations are described here.

(4) Codon Derivatives for the Knob Variation

The requirements of the codon derivatives used in the knob RT are;

1) the codon derivatives must be covalently or non-covalently associated with the RTEs, 2) the association must dissociable and when dissociated, the released codon portion must be amenable to oligonucleotide synthesis (Eckstein, 1991).

3) the codons must be properly protected for downstream oligonucleotide synthesis.

Design and synthesis of codon derivatives and conjugates thereof are enabled by a vast literature of art describing synthesis of nucleotide derivatives and oligonucleotide synthesis, and of bioconjugate chemistry (Eckstein, 1991; Agrawal, 1994; Hermanson, 1996). Codon derivatives for Knob RT are synthesized according to the type of oligonucleotide synthesis is to be performed (phosphoramidite, H-phosphonate, etc.) and the way in which the codon derivative is attached to the RTE. Either RNA or ssDNA maybe be synthesized, depending on the codon structure (DNA does not have a 2' hydroxy ribosyl group but RNA does). The decision regarding whether the product will be RNA or ssDNA will depend primarily upon what type of molecular biology will be performed after PAA-RT is performed.

Figure 9:
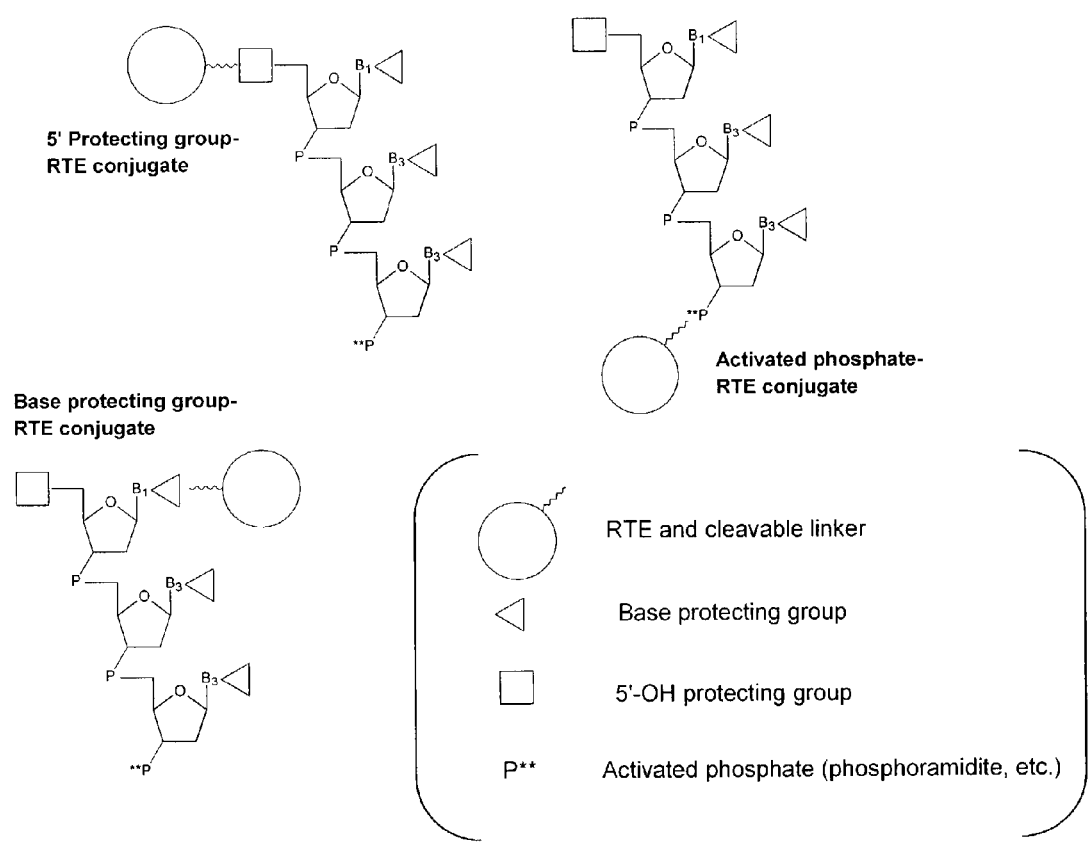
FIG. 9: Examples of potential sites of conjugation in codon derivatives. In Knob RT, the codons may be conjugated to the RTE via one of the illustrated groups. In Displacement and Competitive RT, amino acid derivatives are conjugated to codons via the indicated groups. Shown in this figure, as an illustrative example, is conjugation through the 5' hydroxy protecting group of the codon.
Figure 10:
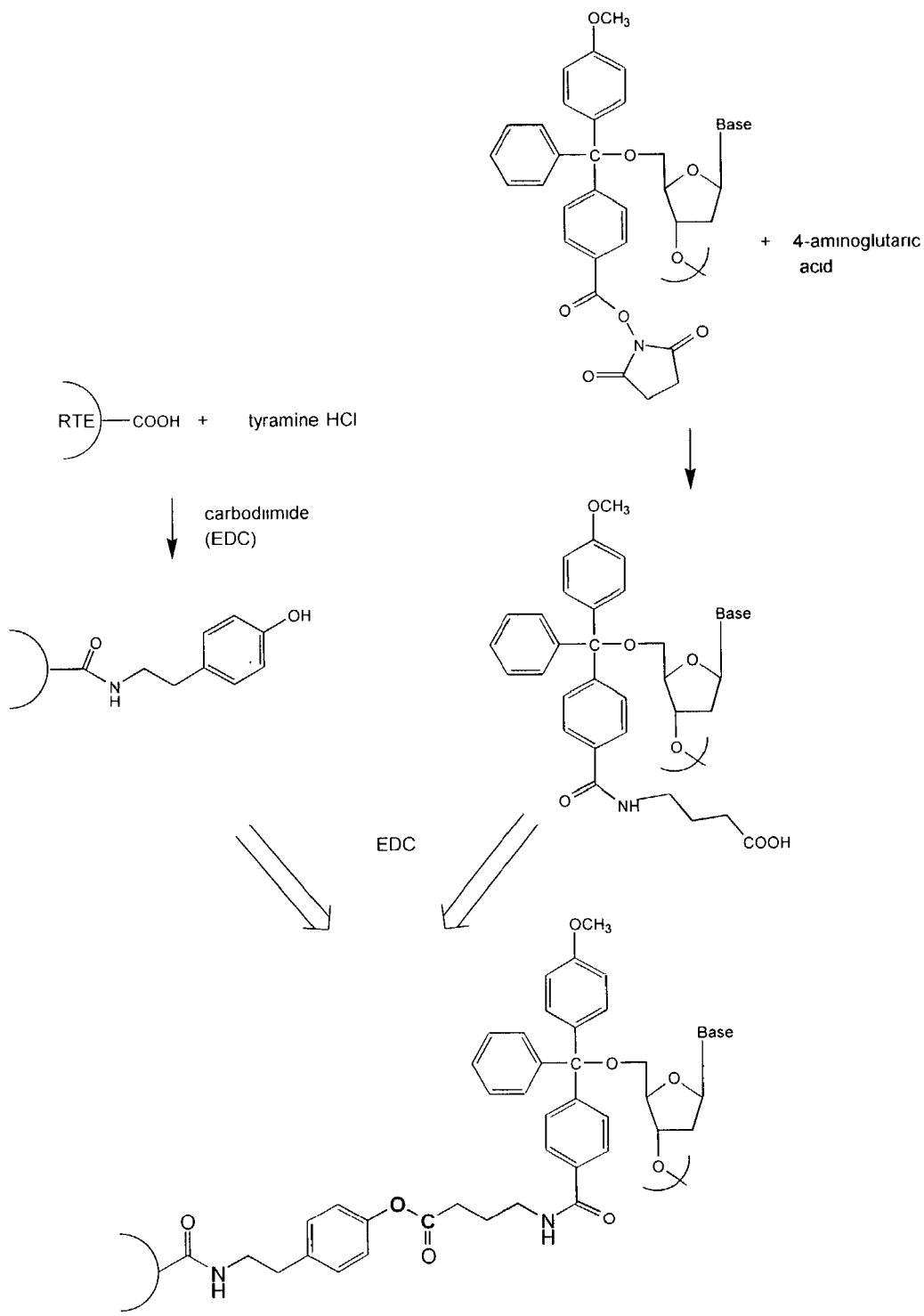
FIG. 10: An example of the conjugation of a codon derivative to a Knob type RTE via a 5'—OH protecting group. The cleavable group is an ester (in bold).
Figure 11:
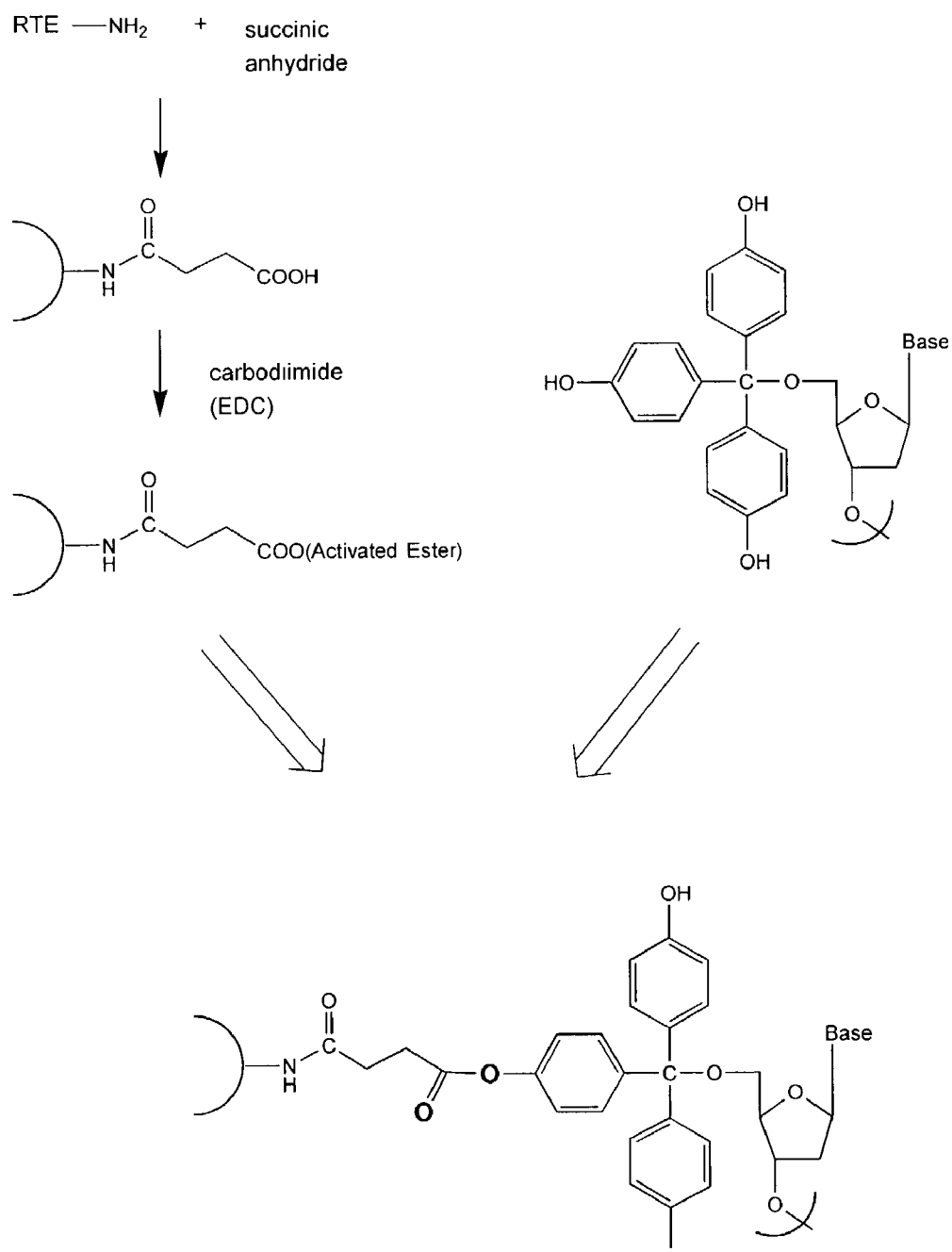
FIG. 11: An example of the conjugation of a codon derivative to a Knob type RTE via a 5'—OH protecting group. The cleavable group is an ester (in bold).

Generic formulas for knob-type codon derivatives are shown in FIG. 9. The illustrated codons have protecting groups, which are normally present during oligo synthesis, and a 3' activating group, used to react with the 5' hydroxyl of a nascent oligo. The figure depicts RTEs covalently coupled to the codon via cleavable linkers. Linkers with typical cleavable groups such as disulfide, ester, or anhydride are well known. Non-covalent links via hydrogen bonds or ionic interactions are also possible. For example, the codon derivatives could bind to antibody-based RTEs or to molecularly imprinted RTEs. For covalently-RTE-linked codon derivatives, the linkage to the RTE can take place via any functional group on the codon or modifying groups. This includes the 3' activating group, the 5' protecting group, a phosphodiester group, a 2' hydroxyl group (if RNA is chosen as the oligonucleotide to be synthesized), or via a nucleotide base. It is especially attractive to have the conjugation link attached to either the 5' protecting group, the 3' activated group, or a base such as thymidine.

PAA-RT can be performed with a variety of oligonucleotide synthesis methods including phosphoramidite, phosphite-triester, and H-phosphonate approaches (Agrawal, 1993). Moreover, the chemistry can be performed in a number of conventional formats including standard automated or non-automated formats and solid phase or solution phase chemistry. These methods, formats, and chemistries are known in the art. The preferred chemistry method is phosphoramidite chemistry which is by far the most common oligonucleotide chemistry used. Several types of phosphoramidite activating groups can be used including the preferred β-cyano-ethyl group (CE). The CE group is preferred because it is most often used and perhaps best understood and convenient.

Figure 8:
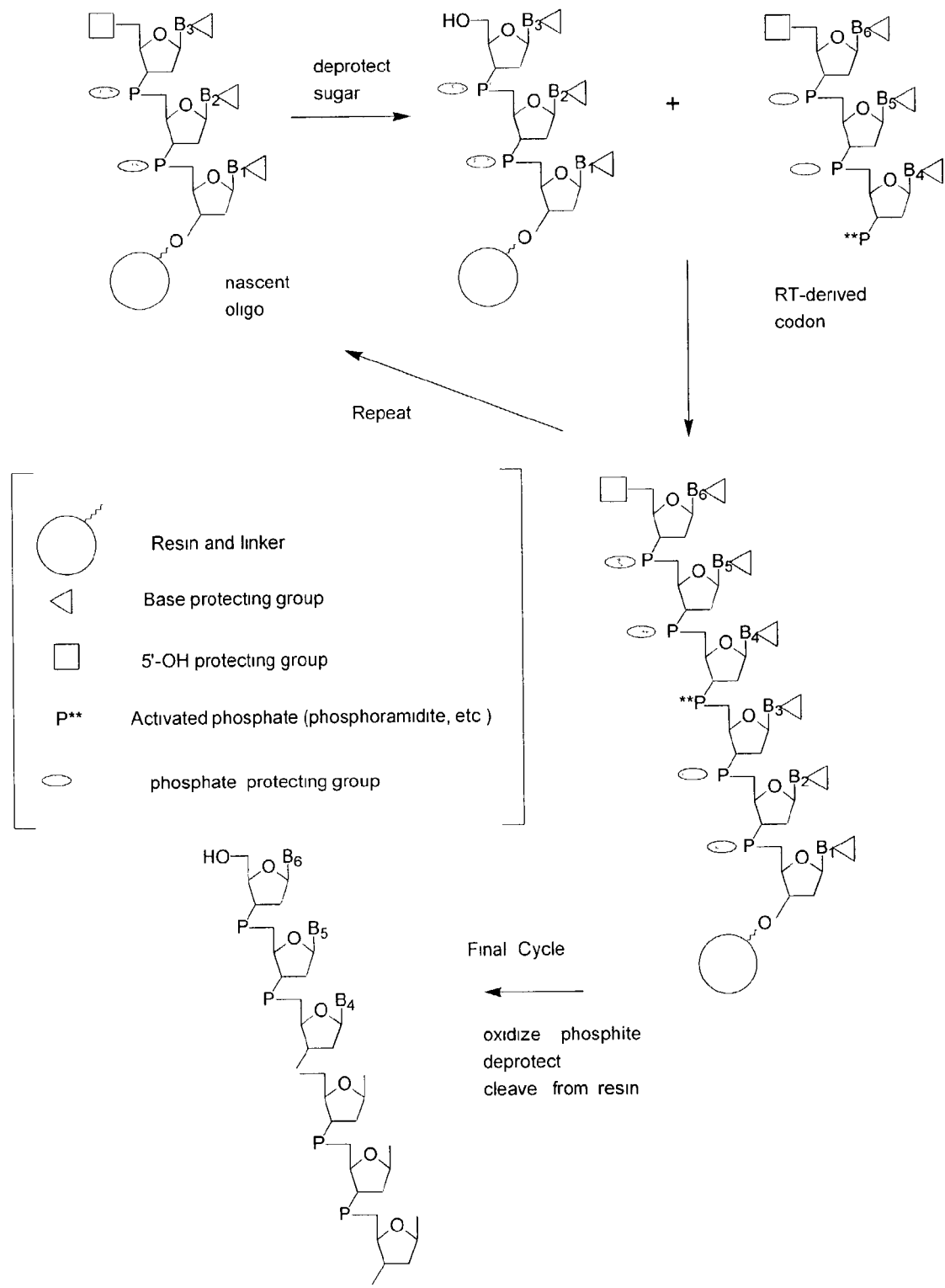
FIG. 8: Scheme showing a typical oligonucleotide synthesis from RT-derived codon derivatives. The well-known step of 5'—OH "capping" is not shown for clarity. Protecting groups will vary as described in the text.

A typical scheme for oligonucleotide synthesis is shown in FIG. 8. Shown here is the scheme for automated phosphoramidite synthesis although other chemistries are equally acceptable. In the case of RT, blocks of three nucleotides (i.e., codons) will be added at a time during synthesis.

Nucleotide bases are usually blocked during oligonucleotide synthesis using conventional protecting groups. These groups would be present on the codon derivatives, as the codon derivatives are subjected to oligo synthesis after the RT step has taken place. Protecting groups are well known for the most common (natural) nucleotides; thymidine, uridine, cytidine, deoxycytidine, adenosine, deoxyadenosine, guanosine and deoxyguanosine. Because these are well known protecting groups and methods for their use are established, I will not provide detailed descriptions, except to indicate typical illustrative publications (Agrawal, 1994; Eckstein, 1991).

In the case of RNA synthesis, there will be a protecting group on the 2'—OH groups of the codon. The identity of the protecting groups will partly depend on the type of chemistry used and will be known to those skilled in the art of oligonucleotide synthesis (Agrawal, 1994, Glen Research, Sterling, Va.).

The identity of the protecting group on the 5'—OH is also not critical. The most often-used group in nucleotide synthesis is DMT (5'—O-dimethoxytrityl-) and that is preferred in RT for the non-covalent type of knob RT. Other usable groups are known in the art (Agrawal, 1994).

Protecting groups for heterocyclic bases, phosphate and 2'—OH groups are known in the art of oligonucleotide synthesis and will not be described at length here. However, it should be pointed out that these groups can are points of covalent attachment of the codon to the RTE. The use of protecting groups is within the knowledge of one skilled in the art.

Numerous well-known nucleotide "modifiers" are commercially available which can be used as RTE-to-codon linkers (Glen Research Corp., Sterling, Va.; TriLink Bio-Technologies, Inc., San Diego, Calif.)). These include 5'- and 3'-modifiers including spacers of various lengths. The 5'-hydroxyl group can be modified with a spacer to give a terminal amino group, phosphate, or thiol. Spacers can be of various lengths and preferably contain polyethylene oxide groups for solubility. The functional group on the far end of the spacer or linker (the end away from the base) would be conjugated to the RTE, via established conjugation chemistry to create a fairly labile bond that could be cleaved, for example by mild NaOH (ester or carbonate) or by an enzyme such as a protease (amide) or by a reducing agent such as dithiothreitol (disulfide linkage). Structures of some of the many possible RTE-codon derivative conjugates are shown in FIGS. 10–13.

Codon Derivatives Non-Covalently Bound to RTEs. Codon Derivatives and RTEs can be made to be complementary in shape and charge so that the codon derivatives bind non-covalently during Knob RT. For example, antibody-derived molecules can be generated against the codon derivatives or MIPs can be imprinted with the codon derivatives. Because in Knob RT the RTE acts as a codon carrier, the binding interaction must have a fairly high affinity (nanomolar Kd or less is preferred). Although specific binding of the codon derivative to the RTE is highly preferred non-specific binding could also accomplish the same task, provided adsorption had high affinity and was reversible.

Non-specific reversible binding would consist of adsorption of the codon derivatives to the material or molecule that the RTE is made from. For example, RTEs may be made from acrylate polymers (imprinted with the Edman amino acid product for capture). Acrylate polymers are known to non-specifically adsorb organic molecules (Yan & Kapua, 2001).

Specific reversible binding could also be the way in which codon derivatives are attached to RTEs. The RTE could for example consist in part of anti-codon derivative antibodies or antibody-derived fragments, which specifically bind the codon derivative. Alternatively, the RTE could consist in part of a molecularly imprinted polymer that specifically binds the codon (and also the Edman product).

So-called non-covalent Knob codon derivatives are closely based on nucleotide derivatives used in oligonucleotide synthesis. FIG. 9 shows schematically the codon derivative and the structures of some sidegroups. The 3' group will depend on the chemistry used. The 5' group will usually be DMT but can be another group. Other groups, used for protecting nucleotide functional groups are also well-known in the literature (Agrawal, 1994).

Codon Derivatives Covalently Attached to RTEs. The codon derivatives may be covalently attached to the RTEs via cleavable linkers. Cleavable groups include but are not limited to esters, amides, anhydrides, and disulfides. The linkers may be attached to the codon derivative at any point, but it is most attractive to have the linker attached via a protecting group that is present on the codon. Protecting groups are normally present on nucleotides during oligo synthesis. Typically, 3'—OH, 5'—OH, bases, 2'—OH, and phosphodiester groups are chemically modified. Any of these groups is acceptable as a point of covalent attachment to RTEs, provided it does not interfere with downstream (post-cleavage) oligonucleotide synthesis. (For example, the 3'—OH will be carrying a phosphoramidite or other activating group, which makes RTE cleavage through this group more technically challenging.)

Two points of attachment on the codon are especially attractive. One is the 5'—OH protecting group. The other is via a base protecting group, such as a thymine protecting group. Numerous linking chemistries are available which one skilled in the art could devise based on voluminous literature on the subject of organic conjugation chemistry. Some examples of cleavable RTE-codon linker chemistries are illustrated in FIGS. 10–13. Because codons will vary in the base identities, it is simplifying and preferable to use a universal chemistry via the 5'—OH protecting group. All codons would then be attached to their RTEs by the same chemistry. Synthesis of these compounds is not described in detail but could be performed by one skilled in the art based on known literature. Other linker attachment strategies could be carried out by numerous ways by one skilled in the art using known methods.

The point of attachment on the RTE will be highly dependent on the chemistry of the RTE. RTEs will vary widely in their chemical make-up, ranging from proteins (antibody-derived molecules) to molecularly imprinted particles (Odian, 1991; Saunders, 1988). Most commonly, the functional group on the RTE will be either a carboxyl group or a primary amine group. With antibody-based RTEs, the functional group will commonly be glutamic acid (—COOH), aspartic acid (—COOH), cysteine (—SH), or lysine (—NH$_2$). With imprinted acrylate polymers, the functional group will commonly be acrylic or methacrylic acid (—COOH), imidazole (heterocyclic nitrogen)(Mathew & Burchart, 1995; Kempe et al., 1993), or phenol (Kirsch et al., 2000). Chemical modification of protein (Means & Feeney, 1971; Wong, 1991; Hermanson, 1996; Hermanson et al., 1992) and polymer sidechains (Ohkubo et al, 1994; Dhal et al., 1995; Kirsch et al., 2000; Ray & Gupta, 1997) are established technical fields.

Reverse Translation: The "Displacement" Variation

In this section, the Displacement variation of RT will be described in more detail. Displacement RT is in itself a category of RT and as illustrated below there are numerous ways it can be performed.

Displacement RT exploits the concept of "displacement chromatography" (Kloor et al., 2000; Kundu et al., 1995; Schmidt et al., 1999; Freitag & Vogt, 2000; Kalghatgi et al., 1992; Shukla et al., 2000; Frenz, 1996). In Displacement RT, RTEs function as displacement chromatography media. RTEs are solid phase materials with binding sites that recognize both amino acid derivatives and C-AAs in a competitive fashion. Amino acid derivatives generally refer to Edman degradation products, but other terminal amino acid degradation products are also acceptable.

As stated above, Displacement RT uses displacement chromatography in the exchange of amino acids for codons. All anticipated amino acids (usually 20) will be potentially recognized and exchanged by the media. Thus, amino acid-specific RTEs are required for the majority of natural common amino acids. There are about 20 specificities of binding sites, each specifically binding on type of amino acid derivative.

The method uses RTE-containing media such as a chromatography column packing or a surface (planar, such as a thin layer chromatography surface) that contains the appropriate binding sites for the anticipated amino acids. Typical chromatographic media is made of particles where the particles contain the RTEs. In Displacement RT individual RTEs are not captured as "knobs" as they are in Knob RT, but the RTEs are part of a bulk stationary phase. Hence, it is recognized that in Displacement RT individual particles can either be dedicated to a single type of amino acid or they can be multi-functional particles with multiple types of binding sites recognizing different amino acid sidechains. Additionally, because the Displacement RTEs do not have to be physically separated, in the extreme case a monolithic porous column or plane of assorted amino acid binding sites can be used.

The Process of Displacement RT

The basic steps for the Displacement variation of RT are described in this section. In Displacement RT, RTEs are used as follows:

(1) RTEs are prepared with binding sites for all anticipated amino acid derivatives produced by Edman (or other similar) degradation. RTEs also recognize and bind to the amino acid sidechain portion of C-AAs.

(2) A column or similar flow device is prepared with the RTE-containing material. The physical format may be anything suitable to the requirements of RT, including a column, a surface (as a thin layer), or suspended filterable particles.

(3) Either before or after (2) but before RT, the RTE binding sites are loaded to saturation with C-AAs. Binding affinity (Kd) will be micromolar, nanomolar, or lower.

Figure 14:
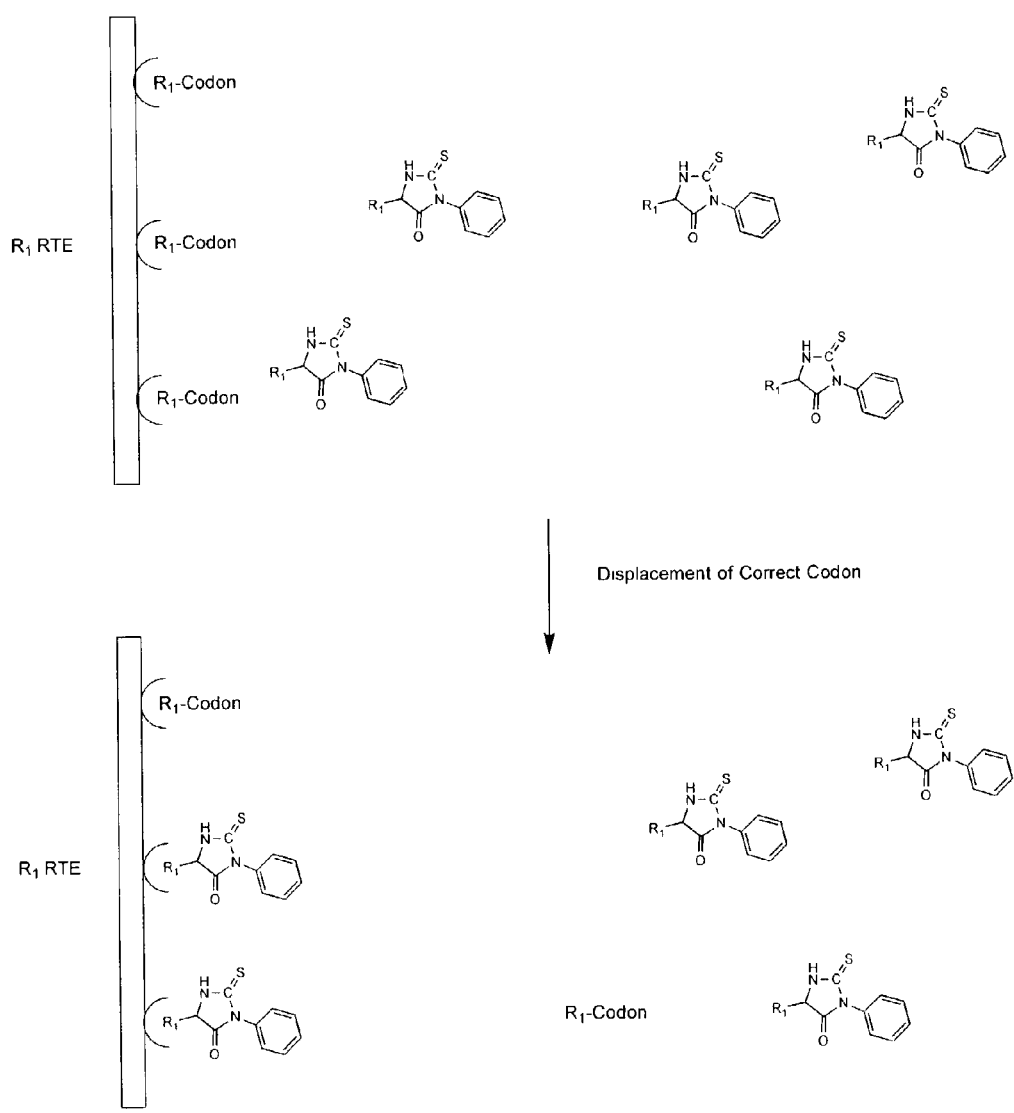
FIG. 14: Illustration of the "Displacement" embodiment of RT.

(4) The eluent from a round of terminal amino acid degradation is added to the RTE collection (column or other format) and allowed to equilibrate. Depending on the type of RTE, the solution may be organic (preferred for MIPs) or aqueous (preferred for antibodies). Because of the competitive nature of binding, the entering amino acid derivative competes with and displaces C-AAs with the same amino acid sidechain structures (FIG. 14). Binding sites are specific enough that displacement results in the predominant displacement of the corresponding C-AA. Binding affinities of the amino acid derivatives and the C-AAs are similar. The displaced C-AA species with the encoding codon is eluted from the column.

(5) The eluted C-AA is added to the growing oligonucleotide chain using conventional oligonucleotide synthesis methods. The amino acid portion of the amino acid-codon conjugate is removed from the codon before or after the codon is added to the growing oligonucleotide chain that encoded the PAA being reverse translated.

(6) The cycle (1–4) is repeated as many times as is required for satisfactory PAA-RT.

Greater detail is provided below for the steps and components mentioned above.

1) Preparation of RTEs

The RTEs can be made from any material that is suitable for displacement or affinity chromatography. Especially attractive are antibodies conjugated to particles or MIP particles or beads. These are attractive for the ease of making specific binding sites required in RT. However, any specific binding sites would be acceptable. Monolithic chromatography is also acceptable, such that all RTEs would be contained in a macroporous monolith.

The RTEs are made using the Edman products, C-AAs, or derivatives thereof. For example, antibodies can be generated to bind to Edman products conjugated to carrier proteins such as bovine serum albumin or keyhole limpet hemocyanin. Alternatively, phage display antibodies can be generated to Edman products. Another example is molecularly imprinted polymers, which can be made to bind specific Edman products. Indeed, amino acid hyantoins, compounds similar in structure to Edman products, have been imprinted (Zhou et al., 1999; Zhou et al., 1999a).

RTEs can be made of molecular imprinted polymers. The polymers are imprinted with amino acid derivatives and are capable of binding amino acid derivatives. The derivatized amino acids may be imprinted separately or together in a single batch. Imprinting will be carried out by methods well know to those skilled in the art. The monomers used will also be conventional imprinting monomers.

Imprinting is often used to create binding sites for small molecules. It can be done in a variety of ways (covalent or non-covalent) using various materials (polymers, silica). The invention is independent of how the polymers were made or what they are made of. The only condition is that they must bind to the PTH amino acids with reasonable affinity (at least some binding sites with nanomolar to micromolar affinities). And they must be sturdy enough to be used in a displacement chromatography procedure (including washes occurring before and after displacement).

2) Physical Format of RTEs During RT

Displacement RT requires a molecular displacement to occur on the surface of a solid phase RTE. The solution phase PAA-derived amino acid derivative is contacted with the solid phase RTE, allowed to incubate for a time sufficient for equilibration to occur, and the solution, containing the displaced C-AA is eluted. Any solid format that allows this to occur is suitable. Some attractive formats include; a packed column of RTEs, a filterable suspension of RTE particles, a membrane containing entrapped RTE particles, and thin layer beds of RTEs.

RTEs may be on or a part of a contiguous single solid material, but for optimized flow properties, it is preferred that RTEs be porous or macroporous particles. The RTEs may be any number of shapes including amorphous particles and spherical beads.

Antibody-coated beads or resin used in Displacement RT are the same as those conventionally used in biochemistry and biotechnology for protein immobilization for immunoassays, affinity chromatography, etc.

3) C-AA Structures

Figure 15:
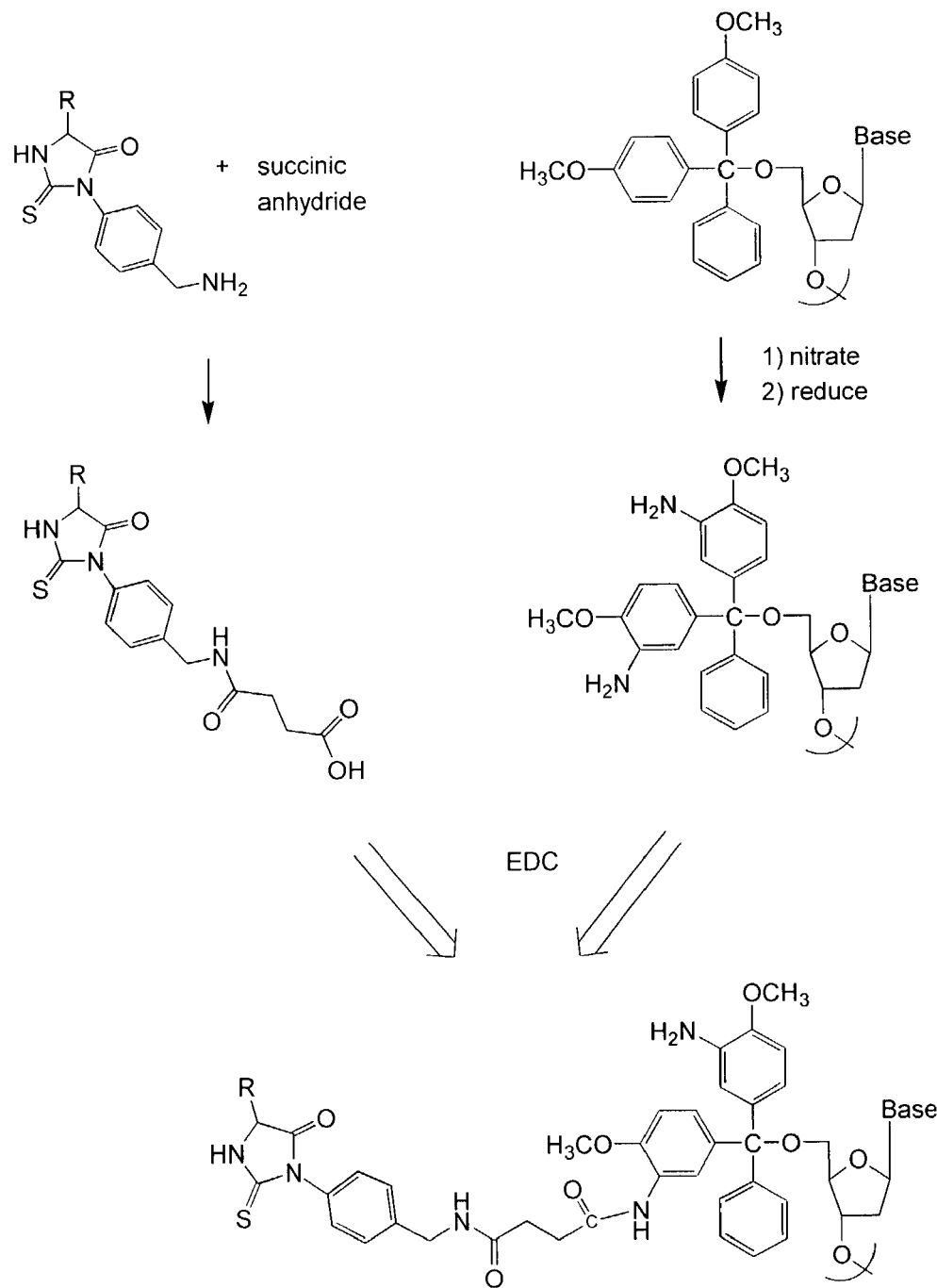
FIG. 15: An illustrative example of the conjugation of an amino acid derivative and the corresponding encoding codon.
Figure 16:
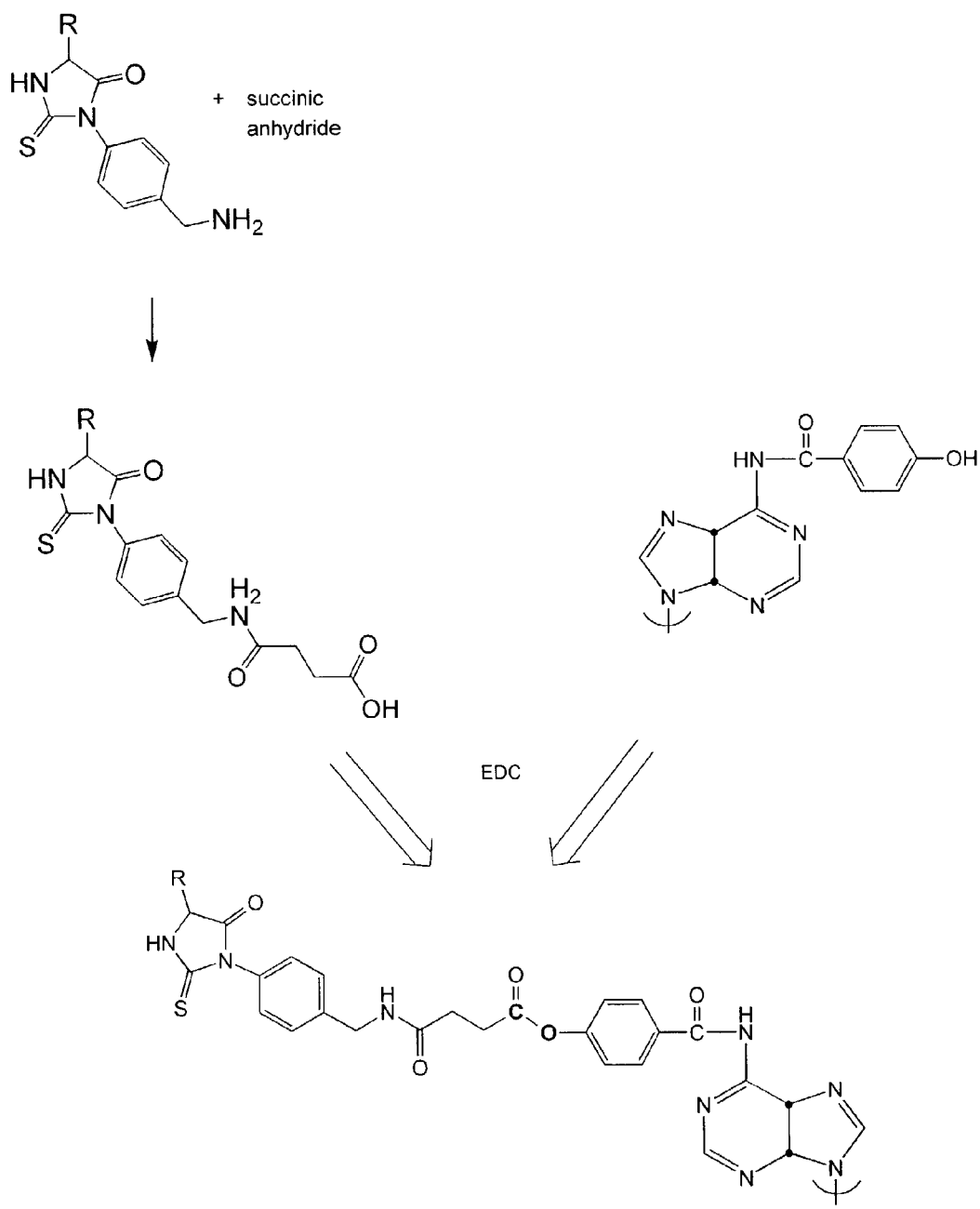
FIG. 16: An illustrative example of the conjugation of an amino acid derivative and the corresponding encoding codon.
Figure 17:
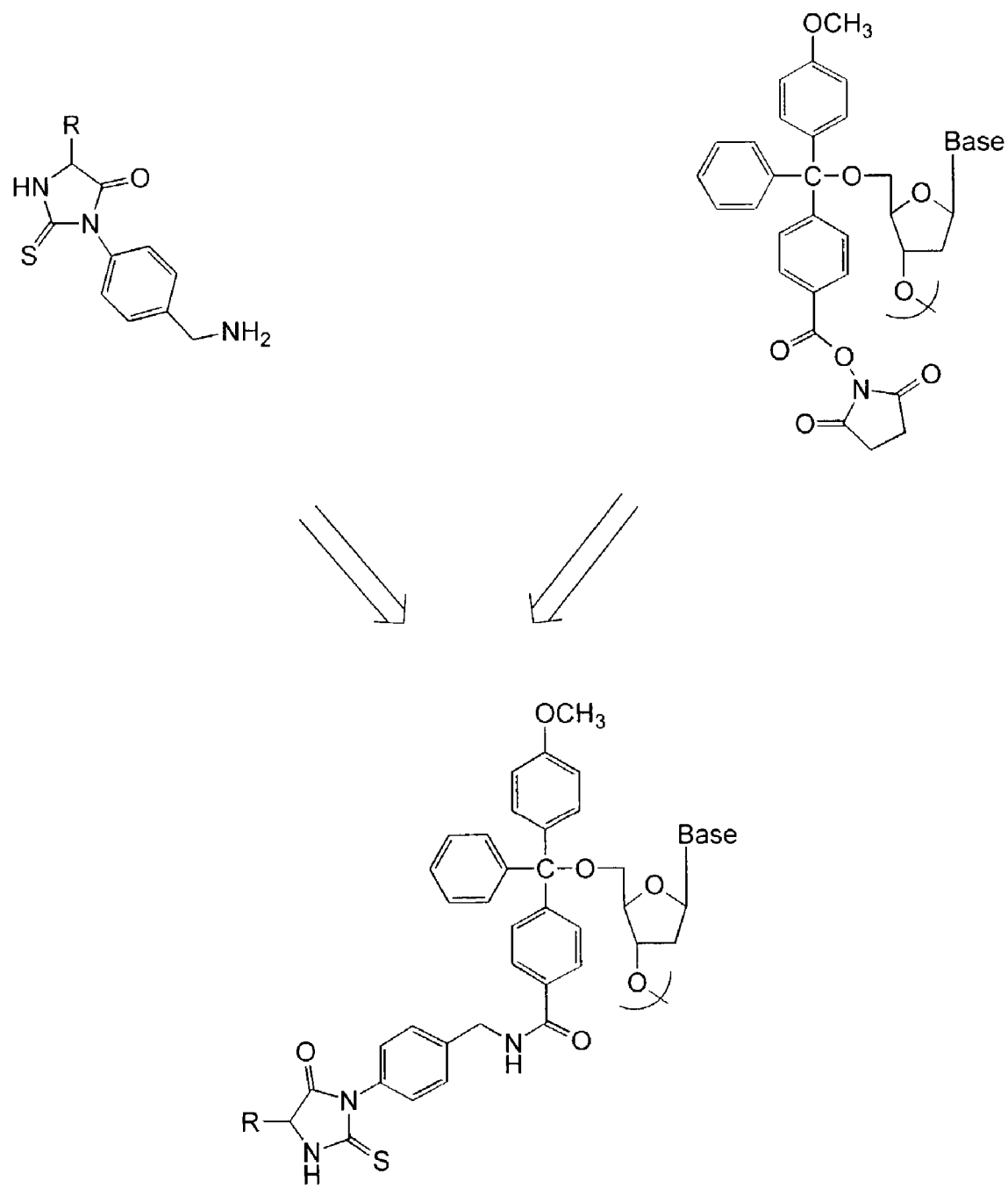
FIG. 17: An illustrative example of the conjugation of an amino acid derivative and the corresponding encoding codon.

Both Displacement and Competitive (see below) RT use C-AAs. The chemical structures of the conjugates contain; a) Edman products, b) cleavable linker, c) a codon which is chemically activated. The coupling method and points of attachment of the codon and amino acid derivative are not critical, but it is preferred that coupling takes place through a protecting or activating group (see above, under Knob RT section). The point of attachment to the degradation product will depend on the type of degradation method used, but will not be through the amino acid sidechain. For PTH amino acids (those created in Edman degradation), attachment points will be in the PTH five-membered ring. Synthesis methods and structures of some acceptable compounds are shown in FIGS. 15–17.

Also, it is not essential and often favored that a compound slightly different for PTH is used in creating the conjugates. Thus, the compound would have the structure; codon-["PTH-like group"]-amino acid sidechain. This concept is illustrated in FIGS. 15–17 where the conjugates are made from aminomethyl PTH compounds. Standard Edman degradation in PAA-RT could be used with these since the PTH amino acid group is the same here as in Edman degradation.

Also, if Edman degradation is not used, but some other form of degradation, then the linkage to the codons would take place through a different group. That group would depend on the degradation method used.

Also, as noted above, degradation products can be modified, for example with a fluorescein group. The codon could be conjugated to this group. (For example, see COOH group in FIG. 5.)

Displacement RT can be verified and optimized using fluorescent amino acid derivatives. For example, to prepare a displacement RT chromatography column containing imprinted sites for the Edman degradation products PTH-glycine, PTH-histidine, and PTH-tyrosine, and use it in the reverse translation of the tripeptide gly-his-tyr, the working column is prepared in the following steps;

(1) three batches of imprinted polymer are made—one batch for each of the three PTH amino acids. (Alternatively, the PTH amino acids can be mixed and imprinted together in a single batch.) PTH amino acids are commercially available (Sigma Chem. Co., and other vendors), (2) Fluoresceinated PTH amino acids are prepared by first forming the aminomethyl PTH derivative (FIG. 4), then labeling the aminomethyl group with N-succinimidyl-ester carboxy fluorescein (Sigma Chem. Co., and other vendors).

(3) Print molecules are washed from the imprinted plastic and the polymer is loaded with a mixture of the correct PTH-amino acid spiked with a small amount of fluoresceinated PTH-amino acid (1000:1 molar ratio, for example).

(4) Displacement chromatography is performed in a small column—for example, in a glass Pasteur pipette or capillary tube. Particles of individual imprinted polymers are packed in the column, and the column is loaded with a combination of PTH-amino acid spiked with fluoresceinated PTH-amino acid. Next, the appropriate PTH-amino acid is added to the column and allowed to elute. Displacement of the fluorescent analog from the column is observed using fluorescence spectroscopy. Conditions (solvent and flow rate) are optimized without undue experimentation to achieve the greatest elution of fluorescent amino acid. Verification and optimization is individually performed for all three imprinted polymers (PTH-gly, PTH-his, and PTH-tyr).

(5) Finally, the three types of imprinted polymer particles (PTH-gly, PTH-his, and PTH-tyr) are mixed and packed into column (loaded with all three PTH-amino acids and traces of their fluorescent derivatives). Each PTH-amino acid is individually chromatographed and conditions are optimized so that a single solvent and flow rate permits specific elution of the fluorescent PTH-amino acid corresponding to the PTH-amino acid that is chromatographed. Elution specificity does not need to be absolute—only to the extent that the major eluting fluorescent species corresponds to the amino acid that is being chromatographed.

Reverse Translation: The "Competitive" Variation

The Knob and the Displacement variations of RT were described above. A third variation is termed Competitive RT. There are multiple ways of carrying out a given step. All embodiments of Competitive RT are considered part of the invention.

Figure 18:
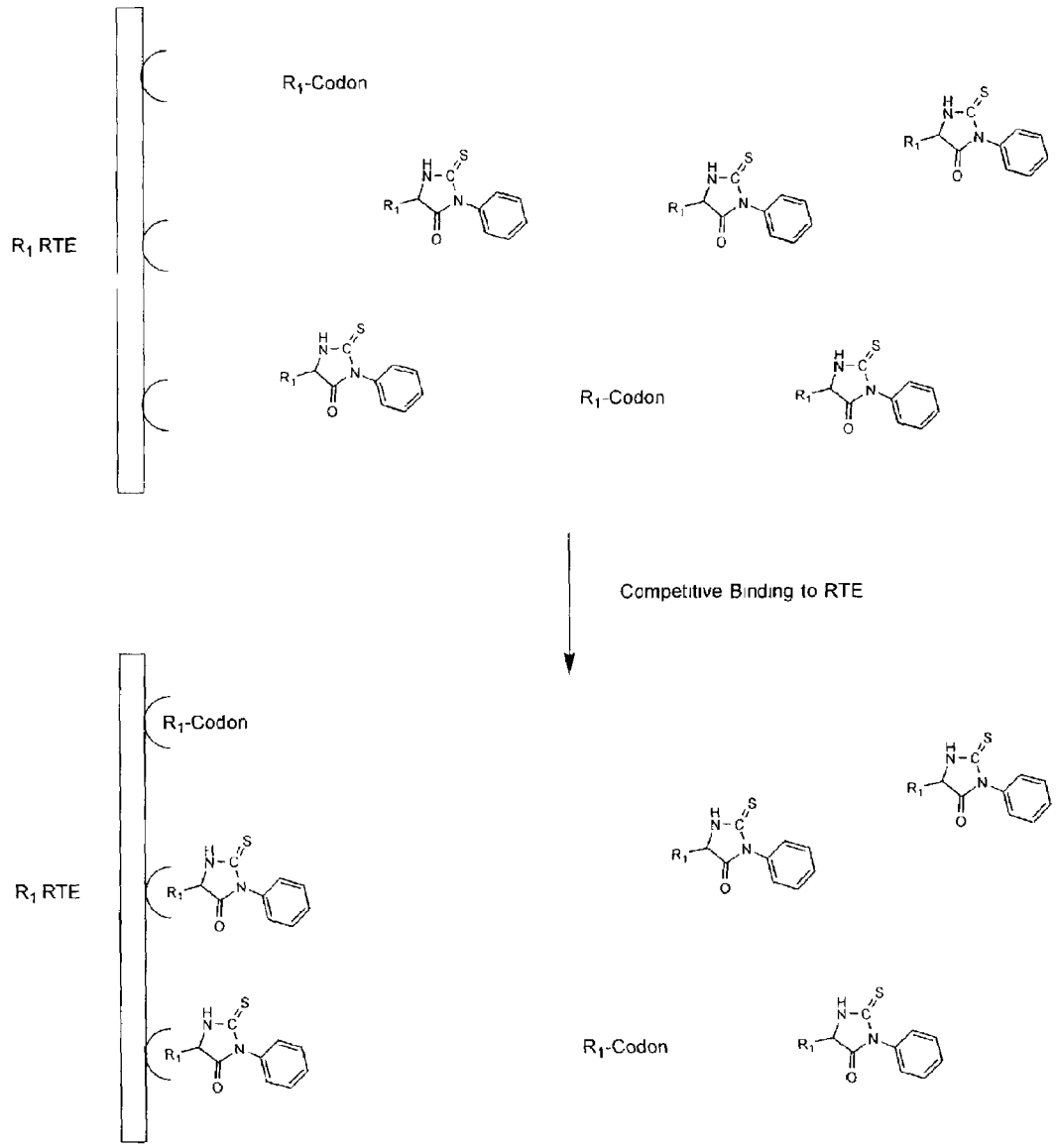
FIG. 18: Illustration of the "Competitive" embodiment of RT.

Competitive RT uses the same type of RTE as is used in the Displacement variation (vide supra). RTEs are prepared prior to RT. As with Displacement RT, Competitive RTEs have, on their surface, specific binding sites for amino acid sidechains. The difference between the Displacement and the Competitive variations of RT is that in the Displacement method, the RTEs are pre-loaded with amino acid-codon conjugates, whereas in the Competitive variation, the PAA cleavage product (amino acid derivative) and the amino acid-codon derivative are added simultaneously (FIG. 18). In the Displacement variation, the PAA product displaces the already bound amino acid-codon conjugate (FIG. 14). In the Competitive variation, the PAA product and the amino acid-codon conjugate compete for binding sites. This so-called "competitive" format of detecting molecules is established in the art (Shiuan et al., 1997), including the use of MIPs as a chromatographic support for competitive chromatography (Vlatakis et al., 1993; Andersson, 2000).

The Process of Competitive-Type RT

The basic steps for the Competitive RT are described in this section. In Competitive RT, RTEs are used as follows:

(1) RTEs are prepared with binding sites for all anticipated amino acid derivatives produced by Edman (or other similar) degradation. RTEs also recognize and bind to the amino acid sidechain portion of C-AAs. [Same as in Displacement RT]

(2) A column or similar flow device is prepared with the RTE-containing material. The physical format may be anything suitable to the requirements of RT, including a column, a surface (as a thin layer), or suspended filterable particles. [Same as in Displacement RT]

(3) The solution containing the amino acid derivative derived from a round of PAA degradation is mixed with a solution of C-AAs representing all anticipated amino acids (normally about 20).

(4) The mixture of amino acid derivative and C-AAs is added to the RTEs. Depending on the type of RTE, the solution may be organic (preferred for MIPs) or aqueous (preferred for antibodies). Both C-AA and the amino acid derivative bind to the RTEs with similar affinities (less than 10 micromolar Kd). The number of binding sites will be roughly equivalent to the number of C-AA molecules. Through competition, the C-AA species corresponding to the PAA-cleavage product will remain in solution, while the C-AAs of irrelevant amino acids will bind to the RTEs (FIG. 18).

(5) The eluted C-AA is added to the growing oligonucleotide chain using conventional oligonucleotide synthesis methods. The amino acid portion of the amino acid-codon conjugate is removed from the codon before or after the codon is added to the growing oligonucleotide chain that encoded the PAA being reverse translated. [Same as Displacement RT]

(6) The cycle (1–4) is repeated as many times as is required for satisfactory PAA-RT. [Same as Displacement RT]

(1) Preparation of RTEs

The preparation of RTEs for Competitive RT is the same as described for Displacement RT.

(2) Physical Format of RTEs During RT

The RTEs for Competitive RT is the same as those described for Displacement RT.

(3) Preparation of Codon Derivatives

The preparation of C-AAs for Competitive RT is the same as described for Displacement RT.

(4) Codon Derivatives

The C-AAs for Competitive RT will be the same as those described for Displacement RT.

Having now generally described the invention, the same will be more readily understood through reference to the following examples, which are provided by way of illustration, and are not intended to be limiting of the present invention, unless specified.

EXAMPLES

Example 1

Preparation of Lysine-Specific MIP-Based RTEs for Knob RT

Knob RTEs can be prepared by the method of molecular imprinting. As can be appreciated by those skilled in the art, MIPs are diverse in structure and composition and there are multiple types that can be used in Knob RT. Knob RTEs:

1) are solid phase particles or microspheres,
2) have binding sites specific for individual amino acid sidechains, and
3) have releasable codon derivatives on the RTE surface.

In chronological order, MIP-based Knob RTEs are made by bulk template polymerization, grinding and filtration to prepare particles, surface attachment of codon derivatives, and removal of the amino acid template (or "print") molecule. Each of these steps is individually described below in the illustrative Example of the preparation of lysine-specific RTEs. Similar preparations can be carried out for other amino acids, with minor modifications such as changes in monomer to reflect the chemical properties of the print molecule. These modifications would not require undue experimentation.

Step 1: Template Polymerization. Lysine peptide specific MIPs have been successfully prepared (Klein et al., 1999; see also Ramstrom et al, 1993) and are the basis for this preparation method.

The print molecule is the fluorescein-modified Edman degradation product of lysine (FIG. 5, Shively, 2000).

To from complementary binding sites to the (positively-charged) lysine sidechain, a polymer made from (negatively charged) methacrylic acid (MAA) is prepared. Polymers are made from the print molecule, the monomers MAA and 2-vinyl pyridine (2VPy), and a crosslinking monomer, ethylene glycol dimethacrylate (EDGMA). The solvent used is acetonitrile. Polymerization is carried out by conventional methods using photoinitiation at 4° C. with azobis-(isobutyronitrile) (AIBN). The total volume of the polymerization mixture is 2 mL.

The optimal ratio of print molecule:MAA:2-Vpy:EDGMA is determined experimentally (Ramstrom et al, 1993) as follows. After Knob particles are prepared (after Step 3 below), binding of the print molecule is determined by the fluorescence of its fluorescein group. The method that gives the polymer with the tightest print molecule binding characteristics is chosen as the method to be used for RTE preparation.

Step 2: Knob Particle Preparation. Imprinted acrylate polymer if made into Knob-sized (capturable) particles. Their size must be small enough to be captured but still large enough to have functional binding sites and bear codons (10 nm–1000 nm). Imprinted polymer is first wrapped in a paper towel and pulverized with a hammer to give polymer pieces no larger than a pea. The pieces are then finely ground using a motorized mortar and pestle. The polymer particles are then added to acetonitrile in a graduate cylinder. The particles are suspended by inversion. The larger particles sediment and the finer particles ("fines") remain suspended. The fines are decanted and dried. Dried fines are resuspended and filtered through a 0.2 µm syringe filter.

Following codon attachment (Step 3), non-covalently bound print molecule is removed by extensive washing.

The ability of the print molecule to bind to MIPs is directly detected. The MIP particles are added to a mixture of fresh print molecule (aqueous) in acetonitrile (1:4 aqueous/acetonitrile). The print molecule is allowed to bind to the MIPs. Following binding and washing to remove non-bound print molecule, binding is detected using fluorescence microscopy and/or flow cytometry. Predominant binding affinities are determined by varying the print molecule concentration and using standard graphical methods (for example, the Scatchard plot).

Figure 12:
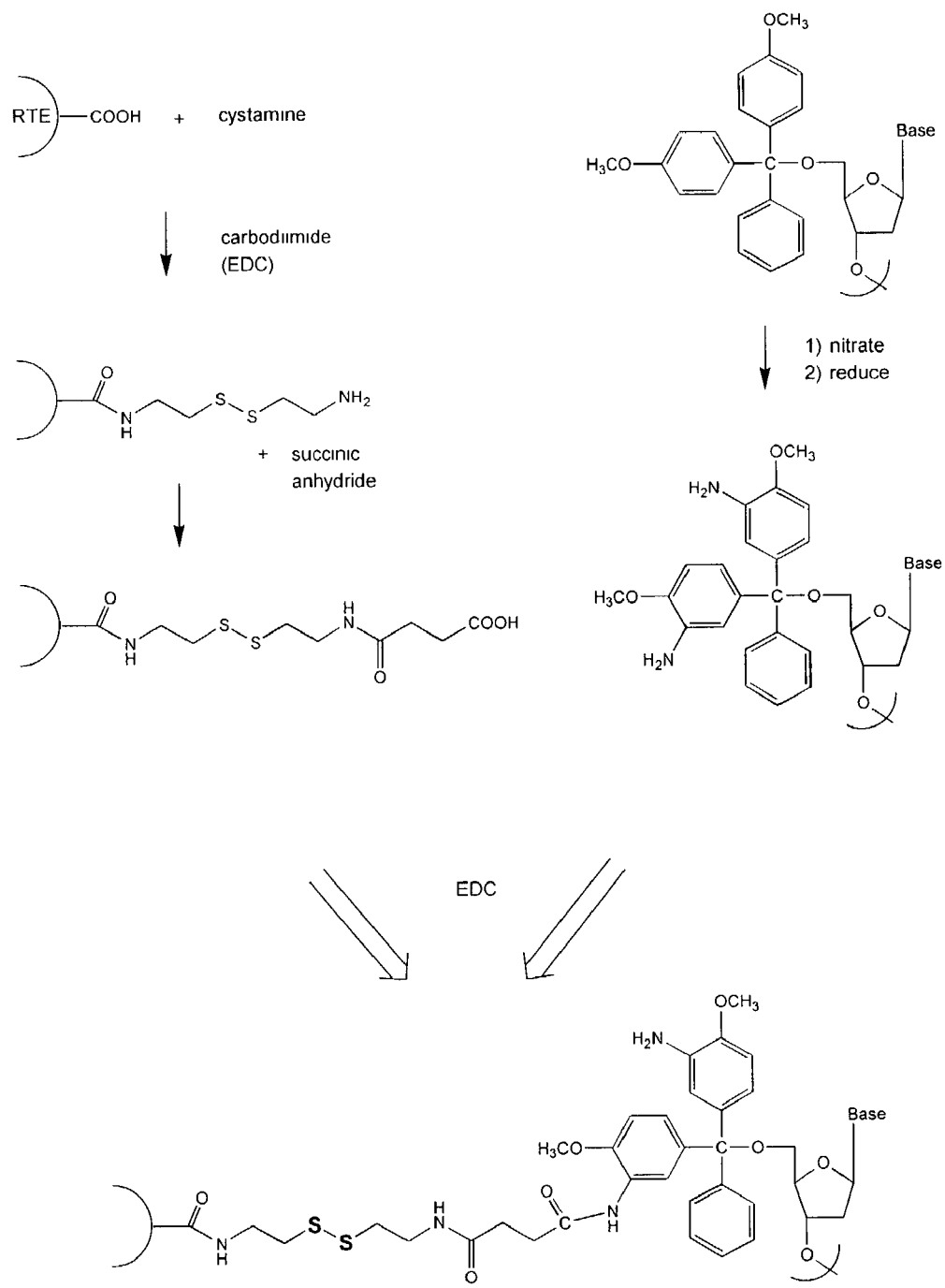
FIG. 12: An example of the conjugation of a codon derivative to a Knob type RTE via a 5'—OH protecting group. The cleavable group is a disulfide (in bold).
Figure 13:
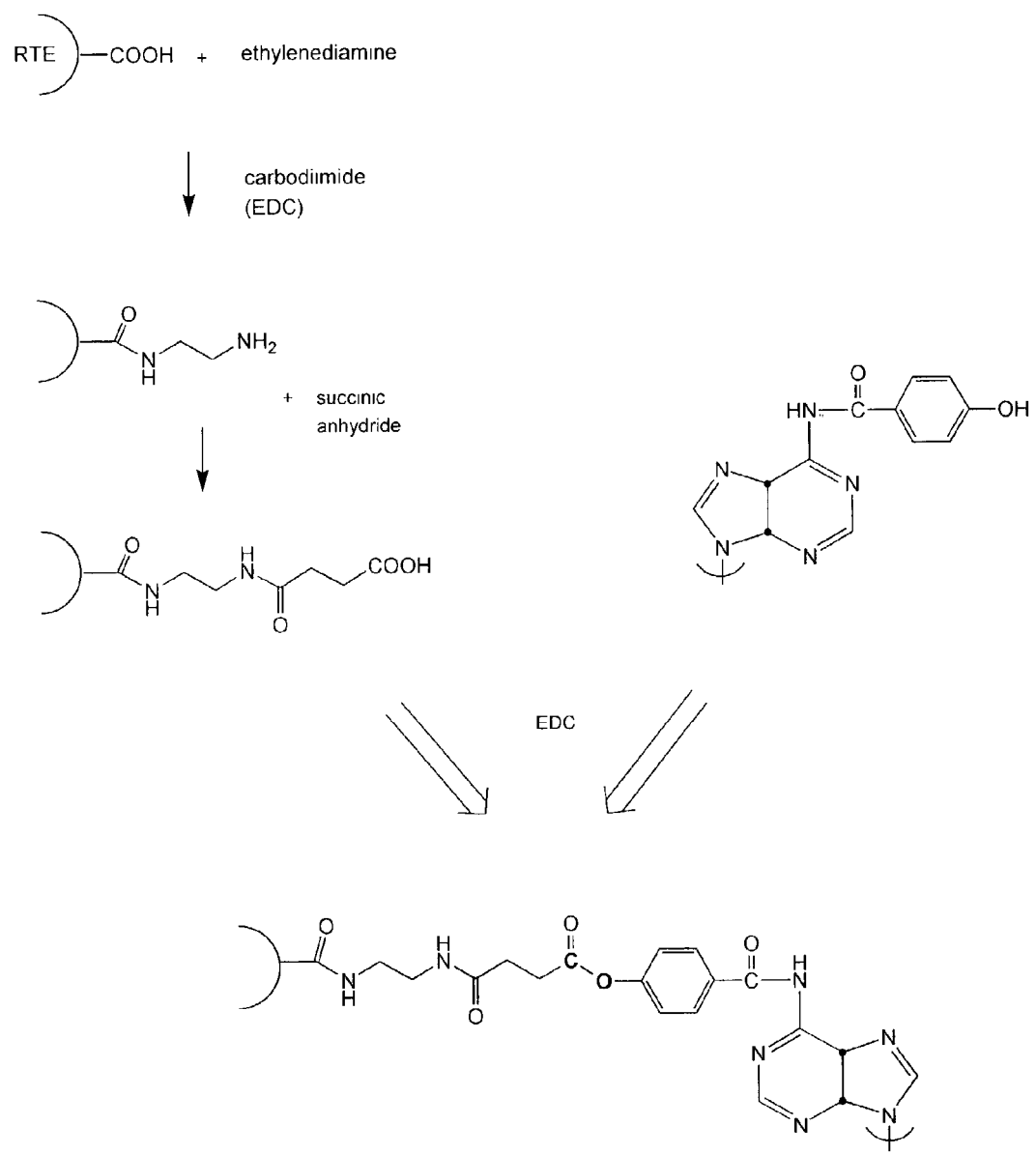
FIG. 13: An example of the conjugation of a codon derivative to a Knob type RTE via an adenine protecting group. The cleavable group is an ester (in bold).

Step 3: Codon Attachment. Preferred codon structure is shown in FIG. 12. Not shown in FIG. 12 is the remainder of the codon structure, which would be a trinucleotide derivative used in conventional oligonucleotide synthesis (3' phosphoramidite). The codon used would be AAA, the predominant codon for lysine (See FIG. 6). Attachment of the codon is shown in FIG. 12 via an RTE —COOH group. This carboxyl group would be the sidechain of RTE surface methyl methacrylic acids groups.

Step 4: Print Molecule Removal. Removal of the template groups is carried out under mild conditions that would not reduce the disulfide bridge and would not destroy the phosphoramidite functional group. The print group is non-covalently associated and will diffuse out of its specific binding pocket with mild perturbations in solvent.

Example 2

Preparation of Antibody RTEs for Knob RT

Step 1: Antibody Preparation. Antibodies take many natural and man-made formats. An attractive format for use in amino acid-binding RTEs is the so-called single chain antibody (also called single chain Fv, or scFv). scFv's are made by phage display methods. Phage display technology involves vast libraries of antibody genes, from which a gene can be chosen for an antibody of choice (Sblattero et al., 2001; Soderlind, et al., 2001; Irving et al, 2001; Paul, 1995). Phage display technology and is commercially available (Amersham Pharmacia Biotech, Invitrogen, New England Biolabs, Novagen, Stratagene, Display Systems Biotech, Cambridge Antibody Technology) as are large scFv antibody gene libraries (Recombinant Phage Antibody System, Amersham Pharmacia Biotech).

Phage scFv's are raised against fluorescein lysine (FIG. 5). Specificity of lysine is determined by comparison of binding with fluorescein arginine and fluorescein glutamate (FIG. 5).

Amino acid-specific scfv's are overexpressed in E. coli. Purification of scFv's is carried out by conventional methods including affinity chromatography on IMAC beads.

Step 2: Immobilization of Antibody on Solid Phase RTE Supports. Solid phase RTE supports are derived from silica IMAC beads (CLONTECH Laboratories, Inc., Palo Alto, Calif.). As provided, the beads are 16–24 µm in diameter and coated with cobalt chelate, which binds polyhistidine-tagged proteins. To make the beads smaller and easier to capture during RT, they are first dried and ground with a mortar and pestle. The resulting powder is then suspended in deionized water. The suspended fragmented beads are filtered through a 0.2 µM PTFE syringe filter. The concentration of immobilized metal in the filtrate (that is, the concentration of binding sites) is determined by atomic absorption spectroscopy. Polyhistidine-tagged scFv is added to the fragmented beads and allowed to bind to saturate the surface binding sites.

Step 3: Codon Coupling to RTEs. The codon derivatives are coupled to the surface of the antibodies by bioconjugate methods (See FIGS. 10–13).

Example 3

Preparation of Codon Derivatives for Knob RT

There are many possible chemical structures for codon derivatives that would be acceptable to Knob RT, some of which are shown in FIGS. 10–13. The required criteria (listed above) include amino acid encoding (typically a trinucleotide), ability to be conjugated to form an oligonucleotide, and ability to be attached to an RTE. Synthesis of these is achievable to one skilled in the art (Hermanson et al., 1992; Hermanson, 1996; Wong, 1991; Guillier et al, 2000). The 3' nucleotide of a trinucleotide codon derivative has a phosphoramidite group for conventional oligonucleotide synthesis (manual or automated). Shown in FIG. 12, the 5' protecting group is coupled to the RTE via an RTE carboxyl group (such as a methacrylate —COOH in a MIP). Synthesis of MIP-based RTEs (codon-conjugated) depicted in FIG. 12 for all codons is carried out by conventional conjugation chemistry methods.

Example 4

Preparation of the Capture Surface for Knob Method RT

The role of the capture surface is to specifically sequester the appropriate RTE. The capture surface accomplishes this via binding of the protruding portion of the bound amino acid derivative (FIG. 7).

Although the capture surface is depicted as a flat surface in FIG. 7, it can be any shape. Indeed, the preferred shape is a bead or particle of substantially larger size than the RTEs. The size difference permits the capture particles to be filtered from the non-bound (inappropriate) RTEs, which are washed away. The capture surface can use any covalent or noncovalent binding mechanism for capture as long as affinity and/or avidity are strong enough to capture the RTEs. The capture surface is "generic" in that it binds to chemical features that all amino acid derivatives have in common. In the current example, the moiety to be bound is the fluorescein group.

If the capture surface is MIP-based, which is the preferred method, the capture surface is made of ground anti-fluorescein MIP particles themselves (see above). Anti-fluorescein MIPs are prepared as described above. Again, MIP binding can be determined by fluorescence of the fluorescein group. If the capture surface is antibody-based, the antibodies are immobilized on IMAC beads such as sold by CLONTECH. MIP-based solid phase extraction matrices have been made for aromatic heterocyclic organic molecules (like fluorescein) including coumarin, theophylline, xanthine, adenine, and caffeine (Mathew and Burchardt, 1995; Ye et al., 1999; Sellergren, 1997). The same procedure is used to extract RTEs from the solution here.

Fluorescein capture is carried out on particles. Although many MIPs compositions would work, one based on methacrylic acid (MAA) monomer is described here (Rachkov et al., 2000; Ye et al., 1999). MAA-based MIPs can bind print molecules with nanomolar affinities (Sellergren, 1997; Ye et al., 1999; Rachkov et al., 2000). MIPS can be made as microspheres (Ye, 1999) or fragments (Rachkov, 2000), as long as they are substantially larger (>>0.2 µm diameter) than the RTEs. Typically, the particles are 25–45 µm in diameter (Rachkov et al., 2000).

Capture particles are made essentially as described in Rachkov et al. (2000). Briefly, template (1 mmol), functional monomer (MAA, 8 mmol), 6 mL of porogen (acetonitrile), 25 mmol of crosslinking agent (EGDMA), and 100 mg of initiator, 2,2'-azobis(isobutyronitrile), are mixed and transferred to a glass vial. The contents are degassed, purged with nitrogen, and sealed. Polymerization is carried out for 16 hours in an oven at 40° C. Polymer is ground in a mortar and pestle and sieved to collect particles of 25–40 µm diameter. Particles are washed six times with ethanol at 60° C. over 24 hours, and then dried in a vacuum.

Affinity and capacity can be measured by the uptake of fluorescein fluorescence of the print molecule.

Example 5

Reverse Translation of Lysine by the Knob Method
  (a) Lysine released by Edman degradation is first modified by fluorescein according to published protocol (Hermanson, 1996; see also Shively, 2000 and Haugland, 1996).
  (b) Fluoresceinated lysine derivative is added to a mixture of RTEs including lysine-specific RTEs. The RTEs are made as described above in Example 1–2.
  (c) Following sufficient time for binding of the lysine derivative to the lysine RTEs, the mixture is added to RTE capture beads (Example 4).
  (d) Following sufficient time for the RTEs to bind to the capture surface, the mixture is filtered through a 0.45 µm filter (PDFE for example). This can be done either in a syringe or filter flask format.
  (e) Codons are released from filter retentate by the addition of a small amount of dithiothreitol (DTT), which reduces the disulfide linkage between the RTE MIP and codon (FIG. 12).
  (f) Released codons are added to solid phase growing oligonucleotide by conventional oligonucleotide synthesis protocols.

Example 6

Preparation of Molecular Imprinted RTEs for Displacement RT

As shown in FIG. 14, Displacement RT is simpler than Knob RT (FIG. 5) in that there is only a single type of binding site (no capture surface is required). What are required are multiple MIPs, one for every type of anticipated amino acid (typically approximately 20). The MIPs are specific for the amino acid side chains and have binding site affinities in the sub-micromolar Kd.

Example 7

Preparation of Antibody RTEs for Displacement RT

Phage scFv proteins are prepared and immobilized on IMAC beads as described in Example 2, Steps 1–2. A difference in Displacement RTEs is that there is little advantage to grinding (fracturing the particles as described in Example 2)—they can be left whole. In addition, alternative IMAC supports can be used such as TALON™ (Sepharose CL-6B), TALON™ Superflow (Superflow), or TALON-spin™ (silica) supports (CLONTECH Laboratories, Inc., Palo Alto, Calif.).

For Displacement RT, antibodies are generated against the fluoresceinated amino acid derivatives (such as lysine). Antibodies are selected which have the highest specificity for individual amino acid sidechains. To do this, for example with lysine, phage are biopanned against the fluoresceinated lysine derivative. Phage that bind are then biopanned against the alanine derivative. Phage that show high selectivity for binding to fluorescein-lysine derivative over the fluorescein-alanine are chosen to be immobilized on beads for RTEs.

Beads with immobilized antibody (scFv) is saturated with amino acid-codon derivatives (Example 8) and gently washed to remove non-specifically bound derivatives.

Example 8

Preparation of Codon Derivatives for Displacement RT

Edman amino acid-codon derivatives are shown in FIGS. 15–17. In the Example described here, fluorescein-lysine Edman derivative is used (see FIG. 5). As can be seen in FIG. 5, fluorescein has a carboxyl group. The conjugation schemes shown in both FIGS. 15 and 16 couple the codon derivative to the amino acid derivative through the amino acid derivative carboxyl group (using EDC coupling). One skilled in the art of bioconjugate chemistry can carry out this conjugation.

Example 9

Reverse Translation of Lysine by Displacement RT (a) Lysine released by Edman degradation is first modified by fluorescein according to published protocol (Hermanson, 1996; see also Shively, 2000 and Haugland, 1996).
(b) Fluoresceinated lysine derivative is added to a mixture of RTEs representing all anticipated RTEs, including lysine-specific RTEs. This can be done in a column, or, more easily, in bulk suspension.
(c) Following sufficient time for displacement of amino acid-codon derivative and rebinding of the lysine derivative to the lysine RTEs, the solution phase is separated from the beads. In the case of a column, the solution phase elutes by flow, in the case of bulk suspension, the solution phase is removed by standard methods of filtration or centrifugation.
(d) Codons are released from RTE are added to solid phase growing oligonucleotide by conventional oligonucleotide synthesis protocols. Because of the leakage of displacement chromatography, a mixture of oligonucleotides will be formed. However, the predominant one will represent the PAA that is being reverse translated.

Example 10

Preparation of Molecular Imprinted RTEs for the Competitive RT

MIP-based RTEs used in Competitive RT are the same as those used in Displacement RT. (See Example 6)

Example 11

Preparation of Antibody-Based RTEs for the Competitive RT

Antibody-based RTEs used in Competitive RT are the same as those used in Displacement RT. (See Example 7)

Example 12

Preparation of Codon Derivatives for the Competitive RT

Codon derivatives used in Competitive RT are the same as those used in Displacement RT. (See Example 8)

Example 13

Reverse Translation of Lysine by the Competitive RT (a) Lysine released by Edman degradation is first modified by fluorescein according to published protocol (Hermanson, 1996; see also Shively, 2000 and Haugland, 1996).
(b) Fluoresceinated lysine derivative is mixed with amino acid-codon derivatives representing all anticipated amino acids. The mixture is added to RTEs that have not been pre-loaded with amino acid-codon derivatives. This italicized phrase distinguishes Competitive RT from Knob RT. The number of binding sites for added amino acid-codon conjugates is equal to or slightly greater than the number of specific binding sites on The RTEs. This can be done in a column, or, more easily, in bulk suspension.
(c) Following sufficient time for competitive binding of (lysine) amino acid derivative and amino acid-codon derivatives to the RTEs, the solution phase is separated from the beads. In the case of a column, the solution phase elutes by flow, in the case of bulk suspension, the solution phase is removed by standard methods of filtration or centrifugation.
(d) The codons in the eluted fraction are added to the solid phase growing oligonucleotide by conventional oligonucleotide synthesis protocols. Because the Edman lysine amino acid derivative will have had competed with its corresponding amino acid-codon derivative, that amino acid-codon will be in higher concentration in the eluted fraction than any other amino acid-codon conjugate. The predominant one will represent the PAA that is being reverse translated.

REFERENCES

Proteomics:
Humphery-Smith et al. (1997) Electrophoresis 18, 1217.
Dove, A. (1999) Nature Biotechnol. 17, 233.
Blackstock, W. P. & Weir, M. P. (1999) Trends Biotechnol. 17, 121.

Reverse Translation (Theory):
Biro, J. (1983) Med. Hypotheses 12, 31
Craig, R. (1981) J. Theor. Biol. 88, 760.
Cook, N. D. (1977) J. Theor. Biol. 64, 113.
Mekler, L. B. (1967) Nature 215, 481–4.
Nashimoto, M. (2001) J. Theor. Biol. 209, 181–187.
Trevors, J. T. (2001) Rivista di Biologia/Biology Forum 94, 105–122.

Protein Chemistry:
Bhown, A. S. (1987) Protein/Peptide Sequence Analysis: Current Methodologies, CRC Press, Boca Raton, Fla.
Lottspeich et al. in Cell Biology: A Laboratory Handbook, 2$^{nd}$ Ed, New York, 1998, J E Celis, ed. P. 304.
Findlay, J B C & Geisow, M J Protein Sequencing. A Practical Approach, Oxford University Press, New York. p. 121.
Dennison, C. A Guide To Protein Isolation. Kluwer Academic, Boston, 1999.
Dupont, D. R. et al. (2000) EXS 88, 119–131.
Freitag, R. & Vogt, S. (2000) J. Biotechnol. 78, 69–72.
Frenz, J. (1996) Meth. Enzymol. 271, 486–504.
Hancock, W. S. CRC Handbook of HPLC For the Separation of Amino Acids, Peptides, and Proteins. CRC Press, Boca Raton, Fla., 1984.
Gevaert, K. et al. (2000) EXS 88, 29–42.
Hellman, U. (2000) EXS 88, 43–54.
Inglis, A. S. (1991) Anal. Biochem. 195, 183–196.
Kalghatgi, K. et al. (1992) J. Chromatogr. 604, 47–53.
Link, A. 2-D Proteome Analysis, Humana, Totowa, N.J., 1999.
Hames, B. D. Gel Electrophoresis of Proteins: A Practical Approach. Oxford Univ. Press, New York, 1998.
Kloor, D. et al. (2000) Clin. Chem. 46, 537–542.
Kundu, A. et al. (1995) Biotechnol. Bioengin. 48, 452–460.
Lahm, H.-W. & Langen, H. (2000) Electrophoresis 21, 2105–2114.
Means, G. E. & Feeney, R. E. (1971) Chemical Modification of Proteins, Holden-Day, San Francisco.
Quadroni, M. & James, P. (1999) Electrophoresis 20, 664–677.
Rabilloud, T. Proteome Research: Two Dimensional Gel Electrophoresis and Identification Methods. Springer, New York, 2000.
Schmidt, B. et al. (1999) J. Chromatogr. A 865, 27–34.
Shiuan, D. et al. (1997) Meth. Enzymol. 279, 321–326.
Shively, J. E. (2000) EXS 88, 99–117.
Shukla, A. A. et al. (2000) Biotechnol. Bioengin. 68, 672–679.
Wang, C. et al. (2000) Rapid Commun. Mass Spectrometry 14, 1377–1383.
Wold, F. (1981) Ann. Rev. Biochem. 50, 783–814.
Wurzel, C. & Wittmann-Liebold, B. (2000) EXS 88, 145–157.

Molecular Imprinting:
Andersson, L. I. et al. (1990a) J. Chromatogr. 516, 323–331.
Andersson, L. I. et al. (1990b) J. Chromatogr. 513, 167–179.
Andersson, L. I. (2000) J. Chromatogr. B 739, 163–173.
Braco, L. et al. (1990) Proc. Natl. Acad. Sci., USA 87, 274–277.
Dai, S. et al. (1999) Angew. Chem. Int. Ed. 38, 1235.
Dhal, P. K. et al. (1995) Chem. Mater. 7, 154–162.
Dickert, F L & Thierer S (1996) Adv. Mater. 8, 987.
Haupt, K. & Mosbach, K. (2000) Chem. Rev. 100, 2495–2504.
Katz, A. & Davis, M. E. (2000) Nature 403, 286–289.
Lee, S.-W. et al. (1998) Chem. Lett. (12) 1193–1194.
Leonhardt, A. & Mosbach, K. (1987) Reactive Polymers 6, 285.
Arnold, F. H. & Sundaresan, V. (1998) U.S. Pat. No. 5,786,428.
Kempe, M. & Mosbach, K. (1995) J. Chromatogr. A 691, 317.
Kirsch, N. et al. (2000) Polymer 41, 5583–5590.
Klein, J. U. et al. (1999) Angew. Chem. Int. 38, 2057–60.
Korhonen, P. et al. (1996) U.S. Pat. No. 5,541,342.
Mallik, S. et al. (1994 New J. Chem. 18, 299–304.
Mathew, J. & Burchardt, O. (1995) Bioconjugate Chem. 6, 524–528.
Andersson et al. (1990) J. Chromatogr. 516, 323.
Mathew-Krotz, J. et al. (1995) J. Am. Chem. Soc. 118, 8134–8135.
Miyahara, T. & Kurihara, K. (2001) Chem. Lett. (12) 1356–1357.
Ngo, T. T. (1993) Molecular Interactions in Bioseparations, Plenum Press, New York.
Odian, G. (1991) Principles of Polymerization, 3$^{rd}$ Ed., Wiley & Sons, New York.
Ohkubo, K. et al. (1994) Polymer 35, 5372–5375.
O'Shannessey, D. J. et al. (1989a) Anal. Biochem. 177, 144–149.
O'Shannessey, D. J. et al. (1989b) J. Mol. Recognition 2, 1–5.
O'Shannessey, D. J. et al. (1989c) J. Chromatogr. 470, 391–399.
Rachkov, A. et al. (2000) Anal. Chim. Acta 405, 23–29.
Ramstrom, 0. et al. (1993) J. Org. Chem. 58, 7562–4.
Ray, A. & Gupta, S. N. (1997) J. Polymer Science: Part A: Polymer Chemistry. 35, 3729–3734.
Saunders, K. J. (1988) Organic Polymer Chemistry, Chapman and Hall, New York.
Shea, K. J. (1994) Trends Polymer Science 2, 166–173.
Shea, K. J. et al. (1993) J. Am. Chem. Soc. 115, 3368–3369.
Shi, H. et al. (1999) Nature 398, 593–597.
Sellergren, B. (1997) Int. Laboratory, July, 10A-10F.
Spivak, D. et al. (1997) J. Am. Chem. Soc. 119, 4388–4393.
Spivak, D. & Shea, K. J. (1998) Macromolecules 31, 2160–2165.
Vlatakis, G. et al. (1993) Nature 361, 645.
Wulff, G. (1998) ChemTech, November, 19–26.
Yan, M. and Kapua, A. (2001) Anal. Chim. Acta 435, 163–7.
Ye, L. et al. (1999) Anal. Commun. 36, 35–38.
Ye, L. et al. (2001) Anal. Chim. Acta 435, 187–196.
Yoshikawa, M. et al. (2001) Macromol. Mater. Eng. 286, 52–59.
Zhou, J., He, X., & Li, Y. (1999) Anal. Commun. 36, 243–6.
Zhou, J., He, X., & Li, Y. (1999) Anal. Chim. Acta 394, 353–359.

Antibody and Phage Display Technology:
Harlow, E. & Lane, D. (1988) Antibodies. A Laboratory Manual, Cold Spring Harbor Laboratory, Cold Spring Harbor, N.Y.
Irving, M. B. et al. (2001) Curr. Opin. Chem. Biol. 5, 314–24.
Paul, S. (1995) Antibody Engineering Protocols, Humana Press, Totowa, N.J.
Sblattero, D. et al. (2001) J. Biotechnol. 74, 303–315.
Soderlind, E. et al. (2001) Comb. Chem. High Throughput Screen. 4, 409–16.

Bioconjugate Chemistry and Oligonucleotide Synthesis:
Product Catalog and technical literature, Glen Research Corporation, Sterling, Va.
Sambrook, J. et al. (1989) Molecular Cloning: A Laboratory Manual 2$^{nd}$ Ed, Cold Spring Harbor, N.Y. Chapter 11. Crosslinkers and Activation.
Guillier, F. et al. (2000) Chem. Rev. 100, 2091–2157.

Haugland, R. P. (1996) Handbook of Fluorescent Probes and Research Chemicals. Molecular Probes, Inc., Eugene, Oreg.

Hermanson, G. T. (1996) Bioconjugate Techniques, Academic Press, New York.

Hermanson, G. T. et al. (1992) Immobilized Affinity Ligand Techniques. Academic Press, New York.

Wong, S. H. (1991) Chemistry of Protein Cross-linking and Crosslinking, CRC Press, Boston.

Eckstein, F. (1991) Oligonucleotides and Analogues. IRL Press, New York.

Agrawal, S. (1993) Protocols for Oligonucleotides and Analogs. Humana Press, Totowa, N.J.

Agrawal, S. (1994) Protocols for Oligonucleotide Conjugates. Humana Press, Totowa, N.J.

Degeneracy:

Honore, B & Madsen, P. (1997) Methods Mol. Biol. 69, 139.

Avers, C. J. (1976) Cell Biology, Van Nostrand, N.Y.

Miscellaneous:

Ahern, K. (2001) Genetic Engineering News 21, 9.

International Human Genome Sequencing Consortium (2001) Nature 409, 860.

Lehninger, A. L. (1975) Biochemistry, $2^{nd}$ Ed., Worth Publishers, Inc. New York.

Salzberg, S. L. et al. (2001) Science 292, 1903–1906.

Sambrook, J. et al. (2001) Molecular cloning: a laboratory manual. Cold Spring Harbor Laboratory Press, Cold Spring Harbor, N.Y.

Venter, J. C. et al. (2001) Science 291, 1304.

All publications and patents mentioned in this specification are herein incorporated by reference to the same extent as if each individual publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A method for synthesizing an oligonucleotide encoding a specific amino acid sequence, said method comprising the steps of:
   (a) contacting an amino acid degradation product from a peptide or protein in a solution with an amino acid binding molecule or particle to which a codon encoding a first amino acid residue is attached,
   (b) allowing said amino acid degradation product to form a specific complex with said amino acid binding molecule or particle,
   (c) contacting said complex with a solid-phase material that captures said complex,
   (d) washing to remove amino acid binding molecules or particles that are not captured by solid-phase material,
   (e) releasing said attached codon from solid-phase captured complex, and
   (f) covalently attaching said released codon to a codon encoding a second amino acid residue to form an oligonucleotide encoding at least two linked amino acid residues.

2. The method of claim 1, further comprising a step of degrading a peptide or protein prior to step(a) to thereby form said amino acid degradation product.

3. The method of claim 1, wherein the amino acid degradation product is added to a solution containing the amino acid binding molecule or particle.

4. The method of claim 1, wherein the amino acid binding molecule or particle is added to a solution containing the amino acid degradation product.

5. The method of claim 1, wherein the amino acid binding molecule or particle comprises a plurality of copies of codons.

6. The method of claim 1, wherein the amino acid binding molecule or particle comprises a plurality of complexation sites for an amino acid degradation product.

7. The method of claim 1, wherein said amino acid degradation product is obtained from a carboxy- or amino-terminal amino acid of a peptide or protein.

8. The method of claim 2, wherein said degrading step is performed by Edman degradation of a peptide or protein.

9. The method of claim 1, wherein said codon has been chemically modified with a moiety selected from the group consisting of phosphoramidite, phosphate-triester, and H-phosphonate.

10. The method of claim 1, wherein said amino acid binding molecule or particle is selected from the group consisting of an antibody-derived molecule and a molecularly-imprinted polymer.

11. A method for synthesizing an oligonucleotide encoding at least two linked amino acid residues of a peptide, said method comprising the steps of:
   (a) contacting a solution containing a plurality of compounds that are conjugates of amino acids and their encoding codons with a plurality of solid phase amino acid binding molecules or particles that contain binding sites that are specific for amino acid sidechains,
   (b) allowing specific complexation of said conjugates to said solid phase amino acid binding molecules or particles, whereby the plurality of compounds are immobilized on the solid phase,
   (c) contacting said immobilized plurality of compounds with a solution containing an amino acid degradation product from a peptide or protein, wherein the amino acid degradation product comprises a derivative of a single type of amino acid,
   (b) allowing the amino acid degradation product to displace conjugates from their specific binding sites on the solid phase amino acid binding molecules or particles, wherein said displaced conjugate has an amino acid whose side chain is the same as the side chain of said degradation product,
   (c) removing the solution containing the displaced conjugates,
   (d) chemically releasing a codon from said removed solution phase conjugates, and
   (e) covalently attaching said released codon to a codon encoding a second amino acid residue to form said oligonucleotide encoding said at least two linked amino acid residues.

12. The method of claim 11, further comprising a step of degrading a peptide or protein prior to step (a) to thereby form said amino acid degradation product.

13. The method of claim 11, wherein the amino acid degradation product is added to a solution containing the said complex.

14. The method of claim 11, wherein the amino acid binding molecules or particles comprise a plurality of complexation sites for amino acid degradation products.

15. The method of claim 11, wherein said amino acid degradation product is obtained from a carboxy- or amino-terminal amino acid of a peptide or protein.

16. The method of claim 12, wherein said degrading step is performed by Edman degradation of a peptide or protein.

17. The method of claim 11, wherein said codon has been chemically modified with a moiety selected from the group consisting of phosphoramidite, phosphate-triester, and H-phosphonate.

18. The method of claim 11, wherein said amino acid binding molecules or particles with attached codons have specific binding sites selected from the group consisting of antibody-derived molecules and molecularly-imprinted polymers.

19. A method for synthesizing an oligonucleotide encoding at least two linked amino acid residues, said method comprising the steps of:
   (a) forming a solution phase mixture of an amino acid degradation product from a peptide or a protein and a plurality of conjugates of amino acid degradation products and their encoding codons, wherein the amino acid degradation product comprises a derivative of a single type of amino acid,
   (b) contacting said mixture with a plurality of solid phase amino acid binding molecules or particles,
   (c) allowing the amino acid degradation product and the conjugate to compete for specific binding sites on the solid phase amino acid binding molecules or particles, and (d) removing the solution phase containing non-bound conjugate and non-bound amino acid degradation product from solid phase amino acid binding molecules or particles,
   (e) chemically releasing the codons from said solution phase conjugates, and
   (f) covalently attaching said released codons to a codon encoding a second amino acid residue to form an oligonucleotide encoding at least two linked amino acid residues.

20. The method of claim 19, further comprising a step of degrading a peptide or protein prior to step (a) to thereby form said amino acid degradation product.

21. The method of claim 19, wherein the amino acid binding molecules or particles comprise a plurality of complexation sites for amino acid degradation products.

22. The method of claim 19, wherein said amino acid degradation product is obtained from a carboxy- or amino-terminal amino acid of a peptide or protein.

23. The method of claim 20, wherein said degrading step is performed by Edman degradation of a peptide or protein.

24. The method of claim 19, wherein said codon has been chemically modified with a moiety selected from the group consisting of phosphoramidite, phosphate-triester, and H-phosphonate.

25. The method of claim 19, wherein said amino acid binding molecules or particles has specific binding sites selected from the group consisting of antibody-derived molecules and molecularly-imprinted polymers.

* * * * *